United States Patent
Morton et al.

(10) Patent No.: US 12,350,369 B2
(45) Date of Patent: *Jul. 8, 2025

(54) SERIAL FILTRATION TO GENERATE SMALL CHOLESTEROL-CONTAINING LIPOSOMES

(71) Applicant: Verily Life Sciences LLC, South San Francisco, CA (US)

(72) Inventors: Stephen Morton, Mountain View, CA (US); Zach Scott, Santa Cruz, CA (US)

(73) Assignee: Verily Life Sciences LLC, Dallas, TX (US)

( * ) Notice: Subject to any disclaimer, the term of this patent is extended or adjusted under 35 U.S.C. 154(b) by 562 days.

This patent is subject to a terminal disclaimer.

(21) Appl. No.: 17/550,935

(22) Filed: Dec. 14, 2021

(65) Prior Publication Data

US 2022/0105037 A1 Apr. 7, 2022

Related U.S. Application Data

(63) Continuation of application No. 16/314,208, filed as application No. PCT/US2017/039777 on Jun. 28, 2017, now Pat. No. 11,246,832.

(60) Provisional application No. 62/355,552, filed on Jun. 28, 2016.

(51) Int. Cl.
*A61K 9/127* (2025.01)
*A61K 9/1277* (2025.01)
*B01D 61/58* (2006.01)

(52) U.S. Cl.
CPC ............ *A61K 9/1277* (2013.01); *A61K 9/127* (2013.01); *B01D 61/58* (2013.01)

(58) Field of Classification Search
CPC ....... A61K 9/127; A61K 9/1277; B01D 61/58
See application file for complete search history.

(56) References Cited

U.S. PATENT DOCUMENTS

| 4,927,637 | A | 5/1990 | Morano et al. |
| 5,008,050 | A | 4/1991 | Cullis et al. |

(Continued)

FOREIGN PATENT DOCUMENTS

| CN | 207440022 | 6/2018 |
| WO | 8600238 | 1/1986 |

(Continued)

OTHER PUBLICATIONS

"Whatman Syringe Filter Collection: Superior performance and choice", GE Healthcare Life Sciences, Product Information, Fisher Scientific, 2007-2011, pp. 1-25.

(Continued)

*Primary Examiner* — Frederick F Krass
*Assistant Examiner* — Amanda Michelle Petritsch
(74) *Attorney, Agent, or Firm* — Kilpatrick Townsend & Stockton LLP

(57) ABSTRACT

The present invention provides methods and systems for producing liposomes by filtration. The methods include passing a heated lipid suspension through a filter assembly comprising two or more filters connected in series, wherein an orifice is disposed between adjacent filters. The methods and systems can produce liposomes having an average diameter that is less than half the diameter of the filter pores. Further, the methods and systems can produce liposomes with <100 nm average diameter, even when the liposomes comprise at least 30% sterol.

6 Claims, 9 Drawing Sheets

(56) References Cited

U.S. PATENT DOCUMENTS

| | | | |
|---|---|---|---|
| 6,001,335 | A | 12/1999 | Unger |
| 6,897,196 | B1 | 5/2005 | Szoka, Jr. et al. |
| 6,930,087 | B2 | 8/2005 | Baru et al. |
| 8,932,498 | B2 | 1/2015 | Ho et al. |
| 10,293,056 | B1 | 5/2019 | Ramesh et al. |
| 2002/0050660 | A1 | 5/2002 | Coe et al. |
| 2003/0003055 | A1 | 1/2003 | Unger et al. |
| 2003/0113369 | A1 | 6/2003 | Martin et al. |
| 2008/0131497 | A1 | 6/2008 | Perkins et al. |
| 2010/0178305 | A1* | 7/2010 | Rapoport ............ A61K 31/513 977/788 |
| 2011/0097389 | A1 | 4/2011 | Sobol et al. |
| 2011/0117026 | A1 | 5/2011 | Tseng et al. |
| 2014/0186430 | A1 | 7/2014 | Gould-Fogerite et al. |
| 2014/0271820 | A1* | 9/2014 | McGhee ................ A61P 11/00 264/4.1 |
| 2015/0174070 | A1 | 6/2015 | Cheng et al. |
| 2015/0315289 | A1* | 11/2015 | Liu ....................... C07K 16/44 424/85.4 |
| 2016/0184433 | A1 | 6/2016 | Kolesnick |
| 2018/0085311 | A1 | 3/2018 | Ekstrom et al. |

FOREIGN PATENT DOCUMENTS

| | | |
|---|---|---|
| WO | 9004943 | 5/1990 |
| WO | 2012088414 | 6/2012 |
| WO | 2018005657 | 1/2018 |

OTHER PUBLICATIONS

U.S. Appl. No. 16/314,208, Final Office Action, Mailed on Jun. 25, 2021, 14 pages.
U.S. Appl. No. 16/314,208, Final Office Action, Mailed on Jun. 22, 2020, 8 pages.
U.S. Appl. No. 16/314,208, Non-Final Office Action, Mailed on Feb. 4, 2021, 12 pages.
U.S. Appl. No. 16/314,208, Non-Final Office Action, Mailed on Feb. 13, 2020, 9 pages.
U.S. Appl. No. 16/314,208, Notice of Allowance, Mailed on Sep. 17, 2021, 6 pages.
Hackbarth et al., "Singlet Oxygen Luminescence Kinetics in a Heterogeneous Environment—Identification of the Photosensitizer Localization in Small Unilamellar Vesicles", Photochemical & Photobiolical Sciences, vol. 14, 2015, pp. 329-334.
Hope et al., "Chapter 8. Reduction of Liposome Size and Preparation of Unilamellar Vesicles by Extrusion Techniques", Liposome technology, vol. 1, 1993, pp. 123-139.
Lu et al., "Profiling Lipid-Protein Interactions Using Nonquenched Fluorescent Liposomal Nanovesicles and Proteome Microarrays", Molecular & Cellular Proteomics, vol. 11, Issue 11, Nov. 2012, pp. 1177-1190.
Application No. PCT/US2017/039777, International Preliminary Report on Patentability, Mailed on Jan. 10, 2019, 7 pages.
Application No. PCT/US2017/039777, International Search Report and Written Opinion, Mailed on Sep. 1, 2017, 11 pages.

* cited by examiner

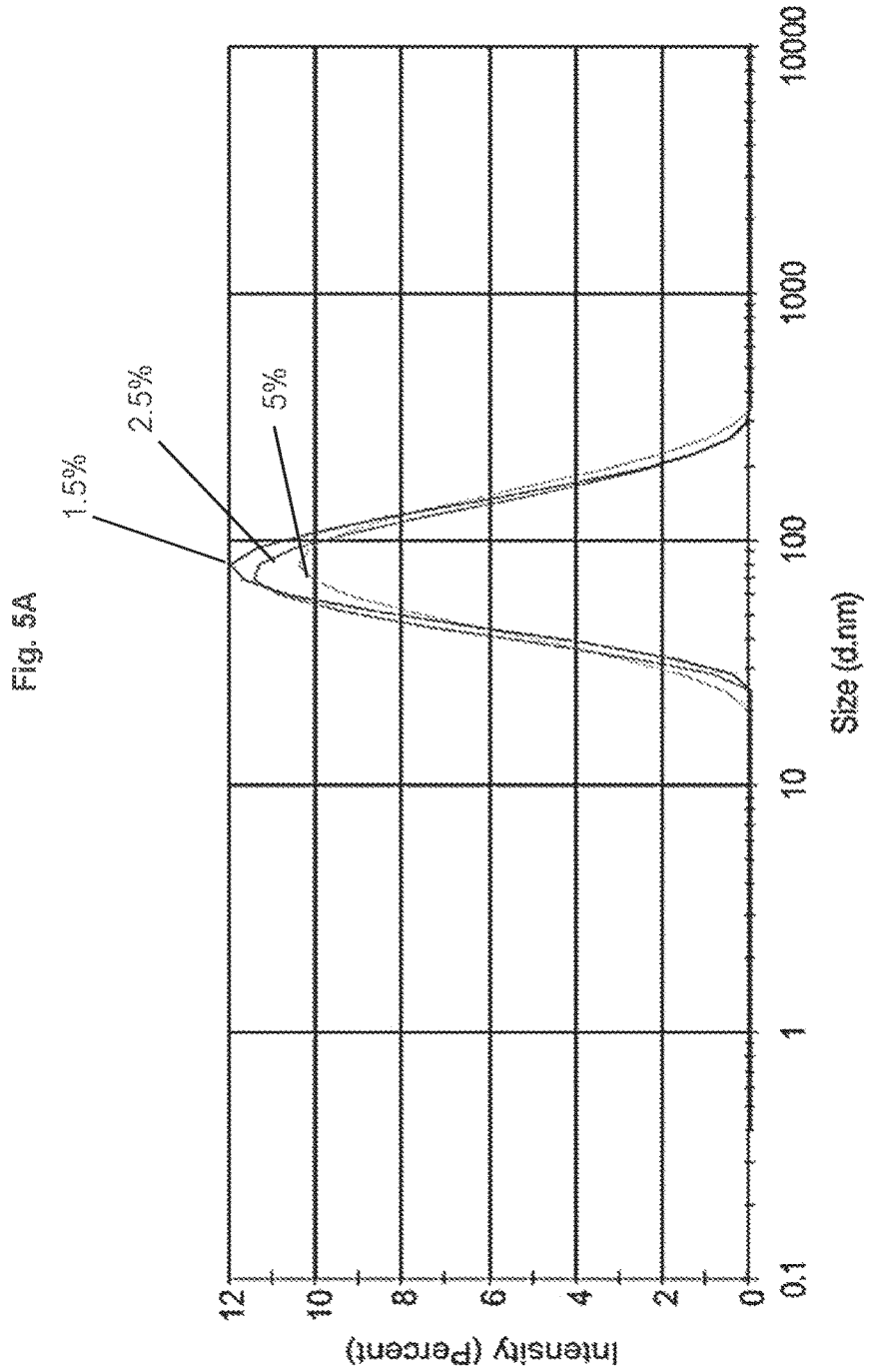

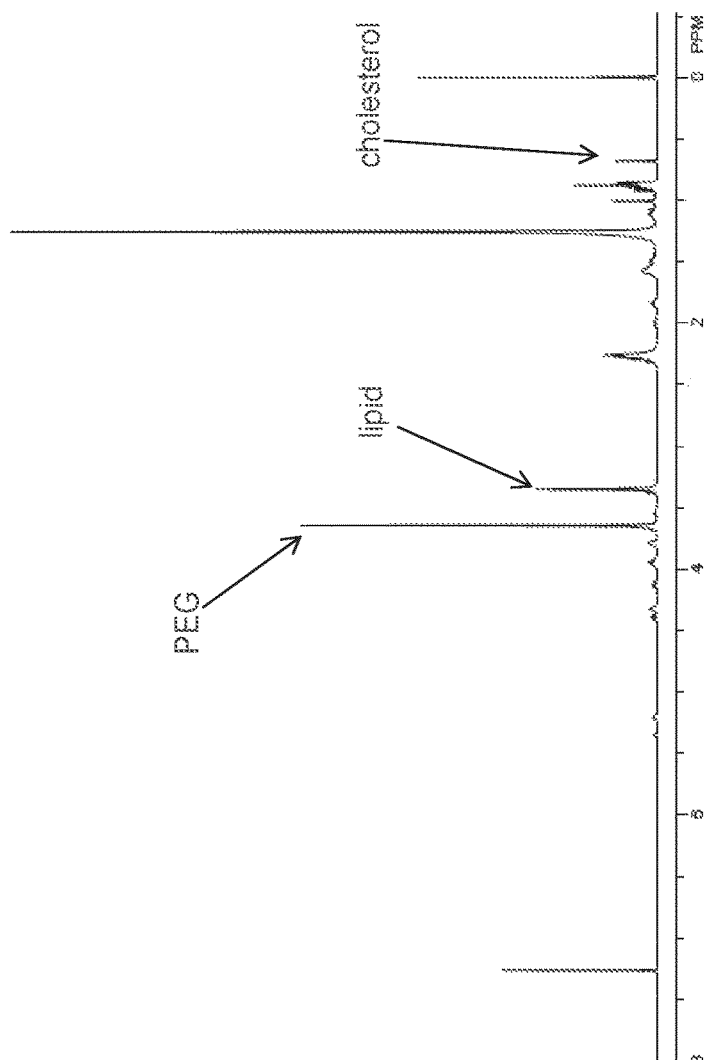

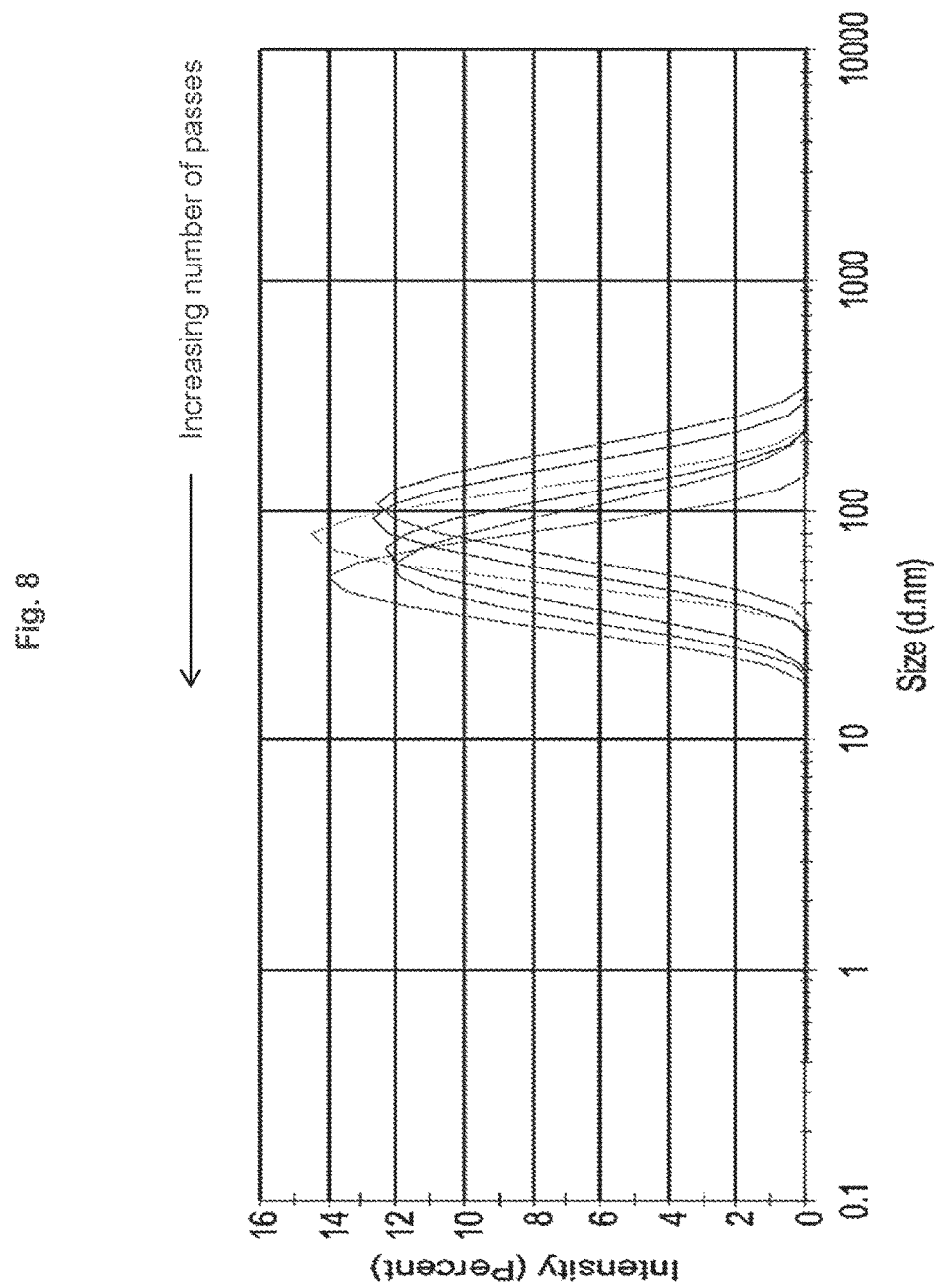

SERIAL FILTRATION TO GENERATE SMALL CHOLESTEROL-CONTAINING LIPOSOMES

CROSS-REFERENCES TO RELATED APPLICATIONS

The present application is a Continuation of U.S. patent application Ser. No. 16/314,208 filed Dec. 28, 2018, which is a 35 U.S.C. § 371 national stage entry of International Pat. Appl. No. PCT/US2017/039777, filed on Jun. 28, 2017, which claims priority to U.S. Provisional Pat. Appl. No. 62/355,552, filed on Jun. 28, 2016, each of which is incorporated herein by reference in their entirety.

BACKGROUND OF THE INVENTION

Nanoparticles are of great interest for future developments in drug delivery in human subjects. The ideal size range of a nanoparticle to maximize bioavailability is between about 20 and about 100 nanometers (nm) in diameter. This size range is above renal clearance but below hepatic fenestration and splenic sinusoidal clearance. Liposomes are of particular interest for delivery of therapeutic agents due to their biocompatibility and their ability to deliver polar and non-polar therapeutic agents. Liposomes suitable for drug delivery often require cholesterol or a cholesterol derivative to hold together the lipid bilayer, in order to prevent lipid ejection and protein penetration that lead to subsequent opsonization and macrophage clearance from the bloodstream. At least around 30 mole percent of cholesterol is typically required for a serum-stable formulation. However, cholesterol-containing liposomes having a diameter of less than 100 nm have proven difficult to prepare.

Existing methods for producing liposomes include extrusion, probe sonication, and bath sonication. Extrusion relies on multiple passes of a lipid suspension from one syringe to another, through a membrane with a given pore size. This method is limited to the production of small batches of liposomes due to flow rate constraints. Further, the membranes are very prone to clogging, resulting in significant material loss and low yield. Also, extrusion is not effective for producing <100 nm liposomes from a lipid suspension comprising significant amounts of cholesterol, such as about 30 mole percent. Probe sonication is not used commercially because probe materials such as titanium can slough off of the probe and contaminate the lipid suspension. Bath sonication has limited power and ability to consistently generate liposomes below 100 nm unless coupled with a second processes step such as syringe filtration or extrusion. Thus, new methods are needed for preparation of uniformly small liposomes containing cholesterol.

BRIEF SUMMARY OF THE INVENTION

In a first aspect, provided is a method of producing liposomes. The method comprises the steps of providing a lipid suspension comprising one or more component lipids; heating the lipid suspension to a temperature which is above the phase transition temperature of the component lipids; and passing the heated lipid suspension through a filter assembly. The filter assembly may comprise two or more filters connected in series with an orifice disposed between adjacent filters. This method can produce liposomes that have a diameter that is significantly lower than the pore size of the filters. For example, in an embodiment, a ratio of the average filter pore size to the average liposome diameter is 1.6 or greater. Liposomes produced by this method can have an average diameter of less than about 100 nm, even when the liposomes comprise cholesterol in amount of at least 30 mole percent. Further, the liposomes can have polyethylene glycol (PEG) brush densities of >100,000 PEG chains per liposome having an average diameter of 100 nm.

In another aspect, provided are liposomes that comprise a sterol in amount of at least 30 mole percent, wherein the average diameter of the liposomes is less than 100 nm. The liposomes may have polyethylene glycol brush densities of >100,000 polyethylene glycol chains per liposome having an average diameter of 100 nm. A population of such liposomes can have a polydispersity index of 0.20 or less.

In another aspect, provided are systems for producing liposomes from a lipid suspension. In some embodiments, a system for producing liposomes from a lipid suspension comprises a filter assembly. In some embodiments, the filter assembly comprises two or more filters disposed in series with an orifice disposed between each pair of adjacent filters. In some embodiments, the system further comprises a component to move the lipid suspension through the filters. The system can have a flow rate of 30 mL/minute or greater. The system does not have to be heated to produce liposomes. Further, the system can be sized for a static volume ranging from small microliter-scale volumes, or less, to thousands of liters, or more. A benefit of serial filtration is that filters with larger pores may be used to generate relatively smaller liposomes, thus preventing filter clogging.

BRIEF DESCRIPTION OF THE DRAWINGS

FIG. 5A shows that changing the PEG loading of liposomes containing DPSE-PEG5000 by varying the mole percent of the PEG lipid does not change the particle size of liposomes, as determined by DLS. DLS data is shown for liposomes containing 1.5 mol %, 2.5 mol %, and 5 mol % DSPE-PEG5000.

FIG. 5B shows the linear control of PEG loading (at 1.5 mol %, 2.5 mol %, and 5 mol %), as determined by NMR.

FIG. 8 shows that average liposome particle size decreases with increasing number of passes through two filters in series, as determined by DLS.

DETAILED DESCRIPTION OF THE INVENTION

Figure 1:
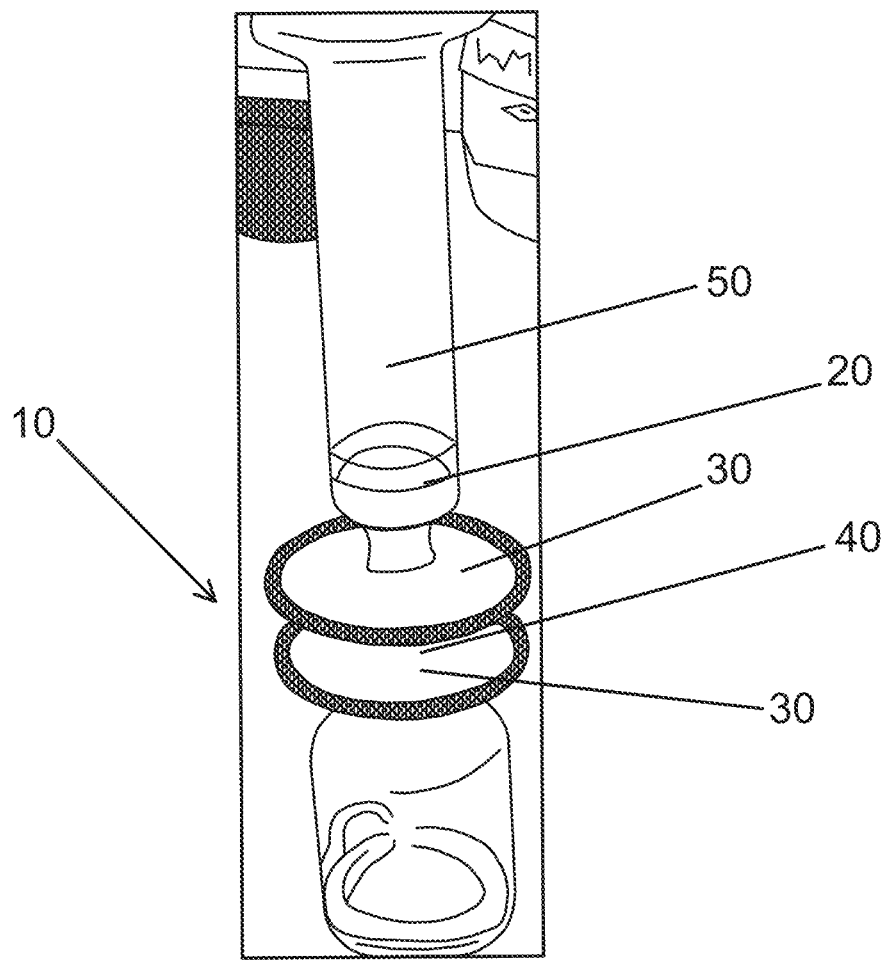
FIG. 1 depicts a system of the invention.

Disclosed are novel methods and systems for consistently producing highly mono-disperse, small-diameter (<100 nm diameter) liposomes having about 20-40 mole percent sterol. Also provided are populations of liposomes generated using the methods and systems disclosed herein. Surprisingly, filtering a cholesterol-containing lipid suspension through filters connected in series with an orifice disposed between adjacent filters provides liposomes that are smaller in diameter and more monodisperse than liposomes prepared with the same number of filters not connected in series. Further, the average diameter of the liposomes produced via serial filtration can be significantly smaller in diameter than the size of the pores of the filters, such as producing 50-nm liposomes by serial filtration through filters having 100 nm pores.

As used herein, the term "liposome" encompasses any compartment enclosed by a lipid bilayer. The term liposome includes unilamellar vesicles which are comprised of a single lipid bilayer and generally have a diameter in the range of about 20 nm to 10 µm. "Small unilamellar vesicles," or SUVs typically range from about 20 nm to about 200 nm in size. Liposomes can also be multilamellar, which generally have a diameter in the range of 1 to 10 µm.

As used herein, the terms "liposome size" and "average particle size" refer to the outer diameter of a liposome. Average particle size can be determined by a number of techniques including dynamic light scattering (DLS), quasi-elastic light scattering (QELS), and electron microscopy.

As used herein, the term "polydispersity index" refers to the size distribution of a population of liposomes. Polydispersity index can be determined by a number of techniques including dynamic light scattering (DLS), quasi-elastic light scattering (QELS), and electron microscopy. Polydispersity index (PDI) is usually calculated as:

$$PDI = \left(\frac{\sigma}{d}\right)^2$$

i.e., the square of (standard deviation/mean diameter).

As used herein, the term "lipid" refers to lipid molecules that can include fats, waxes, steroids, cholesterol, fat-soluble vitamins, monoglycerides, diglycerides, phospholipids, sphingolipids, glycolipids, cationic or anionic lipids, derivatized lipids, and the like. Exemplary liposomes as described in detail below. Lipids can form micelles, monolayers, and bilayer membranes. The lipids can self-assemble into liposomes.

As used herein, the term "amphiphilic lipid" refers to lipid molecules that contain a polar region and a non-polar region. In general, lipids have a polar head group and a non-polar tail group.

As used herein, the term "phosphatidylcholine" refers to a diacylglyceride phospholipid having a choline headgroup (i.e., a 1,2-diacyl-sn-glycero-3-phosphocholine). The acyl groups in a phosphatidylcholine lipid are generally derived from fatty acids having from 6 to 24 carbon atoms. Phosphatidylcholine lipids can include synthetic and naturally-derived 1,2-diacyl-sn-glycero-3-phosphocholines.

As used herein, the term "sterol" refers to a steroid containing at least one hydroxyl group. A steroid is characterized by the presence of a fused, tetracyclic gonane ring system. Sterols include, but are not limited to, cholesterol (i.e., 2,15-dimethyl-14-(1,5-dimethylhexyl)-tetracyclo [8.7.0.0$^{2,7}$, 0$^{11,15}$]heptacos-7-en-5-ol; Chemical Abstracts Services Registry No. 57-88-5).

As used herein, the term "PEG-lipid" refers to a poly (ethylene glycol) polymer covalently bonded to a hydrophobic or amphiphilic lipid moiety. The lipid moiety can include fats, waxes, steroids, fat-soluble vitamins, monoglycerides, diglycerides, phospholipids, and sphingolipids. For example, the PEG-lipid may be a diacyl-phosphatidylethanolamine-N-[methoxy(polyethylene glycol)] or an N-acyl-sphingosine-1-{succinyl[methoxy(polyethylene glycol)]}. The molecular weight of the PEG in the PEG-lipid is generally from about 500 to about 5000 Daltons (Da, g/mol). The PEG in the PEG-lipid can have a linear or branched structure.

As used herein, the term "PEG brush density" refers to the number of PEG chains extending from the surface of a liposome, expresses as a function of liposome size. For example, a population of 100-nm liposomes having on average 10,000 PEG chains per liposome has a PEG brush density of 10,000 PEG chains per 100 nm liposome.

As used herein, the terms "molar percentage" and "mol %" refer to the number of a moles of a given lipid component of a liposome divided by the total number of moles of all lipid components. Unless explicitly stated, the amounts of active agents, diluents, or other components are not included when calculating the mol % for a lipid component of a liposome.

As used herein, the term "composition" refers to a product comprising the specified components in the specified amounts, as well as any product which results, directly or indirectly, from combination of the specified components in the specified amounts. Lipid compositions of the present invention generally contain a sterol and are pharmaceutically acceptable. By "pharmaceutically acceptable," it is meant that the carrier, diluent, or excipient must be compatible with the other components of the formulation and non-deleterious to the recipient thereof.

As used herein, the term "porous filter" refers to a polymeric or inorganic membrane containing pores with a defined diameter (e.g., 50-500 nm). Porous filters can be made of polymers including, but not limited to, polycarbonates and polyesters, as well as inorganic substrates including, but not limited to, porous alumina.

As used herein, the term "filters connected in series" refers to two or more filter membranes that are placed near each other and separated by some distance. Therefore, a fluid flowing through the filters would flow through a first filter and then flow through additional filters in sequence.

As used herein, the term "orifice" refers to a physical feature such as an orifice, hole, opening, aperture, slit, or slot disposed between two filter membranes. As used herein, the orifice generally has a cross-sectional area that is smaller than the average cross-sectional area of the adjacent filter membranes. An orifice can be contained in a system component such as a filter housing fully enclosing a filter membrane, or a panel (e.g., a disc or other shape) placed between filter membranes but not enclosing the filter membranes.

As used herein, the term "static volume" refers to the volume of fluid required to fill an assembly or system when the fluid is not moving through the system.

As used herein, the terms "delivery" and "delivering" refer to conveyance of a therapeutic agent to a subject using the methods of the invention. Delivery may be localized to a particular location in a subject, such as a tissue, an organ, or cells of a particular type.

As used herein, the term "therapeutic agent" refers to a compound or molecule that, when present in an effective amount, produces a desired therapeutic effect in a subject in need thereof. The present invention contemplates a broad range of therapeutic agents and their use in conjunction with the liposome compositions.

As used herein, the term "subject" refers to any mammal, in particular a human, at any stage of life.

As used herein, the term "consists essentially of" refers to a composition having the stated components, in addition to minor components (e.g., unavoidable impurities) that do not materially affect the properties of the composition (e.g., the average size or monodispersity of a population of liposomes).

As used herein, the term "about" indicates a close range around a numerical value when used to modify that specific value. If "X" were the value, for example, "about X" would indicate a value from 0.9X to 1.1X, e.g., a value from 0.95X to 1.05X, or a value from 0.98X to 1.02X, or a value from 0.99X to 1.01X. Any reference to "about X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X, and values within this range.

I. METHODS

In a first aspect, provided is a method of producing liposomes. The method may comprise the steps of providing a lipid suspension comprising one or more component lipids; heating the lipid suspension to a temperature which is above the phase transition temperature of the component lipids; and passing the heated lipid suspension through a filter assembly. The filter assembly may comprise two or more filters connected in series with an orifice disposed between adjacent filters. The method allows for the reproducible production of liposomes of controlled diameter with defined polydispersity.

Each filter may comprise a porous membrane containing pores with a specified diameter or pone size. The filter pore diameter or pore size may be any size suitable for producing nanoparticle liposomes (e.g., 50-500 nm). For example, the filter pore diameter or pore size can be from 50-100 nm, from 100-200 nm, or from 200-500 nm. In some instances, the filter pore diameter or pore size can be around 100 nm.

The porous filter membranes can be made of any inert material. In certain embodiments, the filter(s) may comprise polymers including, but not limited to, polycarbonates and polyesters. For example, the porous filters may comprise GHP (hydrophilic polypropylene), PES (polyether sulfone). Nylon, or PVDF (polyvinylidene fluoride). Additionally and/or alternatively, the filter(s) may comprise inorganic substrates including, but not limited to, porous alumina or glass fiber. In some embodiments, the filter membranes are enclosed in a housing.

The filter assembly can contain two, three, four, five filters, and optionally additional filters. In some embodiments, the filters are syringe filters. In some cases, the filters are syringe-tip filters such as an Acrodisc syringe filter with a Supor membrane (e.g., 13 mm diameter, 25 mm diameter, or 32 mm diameter) sold by Pall Corporation, Port Washington, NY The filters may be connected in series, with two or more filter membranes facing each other and separated by a distance typically ranging from a few microns to several millimeters or more. In this way, a fluid flowing through the filters would flow through one filter, flow through an orifice disposed between the filters, and then flow through the additional filter(s). The distance between the filters can be any distance greater than about 1000 nm. In certain embodiments, the membranes may be separated by 1 mm, 1 cm, 100 cm, or more. In general, the filter membranes are not stacked directly one on top of the other and do not touch each other.

In various embodiments, at least one orifice is disposed between adjacent filters. The orifice is disposed between two adjacent filter membranes so as to constrict the flow of fluid (e.g., the lipid suspension). In various embodiments, the orifice is a hole, opening, aperture, slit, slot, or any similar means for constricting or narrowing the diameter of the fluid stream as the fluid flows from an upstream filter to a downstream filter. Therefore, the orifice has a diameter (or cross-sectional area, if not round) that is smaller than the average diameter (or cross-sectional area) of the adjacent filter membranes.

Not intending to be bound by theory, it is believed that the constriction of the fluid stream between two adjacent filters introduces shear forces that promote formation of smaller liposomes than would have been formed by passing the same lipid suspension twice through a single filter. The resulting liposomes are also smaller liposomes than those produced by passing the same lipid suspension through two filters that are not connected, or that are connected without an orifice disposed between. Similarly, liposomes produced by filtration through 3 filters in series will be smaller than liposomes produced by filtration through 3 filters that are not in series, liposomes produced by filtration through 4 filters in series will be smaller than liposomes produced by filtration through 4 filters that are not in series, liposomes produced by filtration through 5 filters in series will be smaller than liposomes produced by filtration through 5 filters that are not in series, and so on. In some examples, the diameter or cross-sectional area of each orifice disposed between two adjacent filters is less than or equal to about 1%, 5%, 20%, 50%, 70, or 80% of the average diameter or cross-sectional area of the filters adjacent to the orifice. In some embodiments, the diameter or cross-sectional area of each orifice disposed between two adjacent filters is less than or equal to 70% of the average diameter or cross-sectional area of the filters adjacent to the orifice.

As described in detail below, for example, one pass of a lipid suspension through 4 filters with orifices disposed between the filters yielded liposomes having an average diameter of 60.49 nm and a polydispersity of 0.084, whereas passing the lipid suspension through four membrane filters stacked with no intervening orifices yielded liposomes with an average diameter of 88.25 nm and a polydispersity of 0.150. These results occurred even though each lipid suspension was passed through the same number of filters.

Previously known systems for liposome preparation often require the application of significant pressure to force lipid suspensions through filters. In contrast, the filter assembly disclosed herein does not require significant pressurization to force the lipid suspension through the filter membrane. Although a small amount of pressure, e.g., around 100 pounds per square inch (psi), can inherently build as the fluid flows or is pushed through the filter assembly, the method generally does not require applying higher pressures, e.g., 300 psi, 500 psi, 1000 psi, or greater, as required by many previously-known methods. In some embodiments, the pressure in the filter assembly is less than 300 psi, less than 200 psi, or less than 100 psi.

In some embodiments, a lipid suspension is prepared by adding the desired lipids in the desired molar ratios to an aqueous solvent, and then providing mechanical energy sufficient to suspend the lipids in the aqueous solvent. The mechanical energy may be supplied by shaking, stirring, sonicating, or other similar methods.

The lipid suspension can contain any suitable lipid, including neutral lipids, cationic lipids, anionic lipids, and/or zwitterionic lipids. Suitable lipids can include fats, waxes, steroids, sterols, cholesterol, fat-soluble vitamins, monoglycerides, diglycerides, phospholipids, sphingolipids, glycolipids, cationic or anionic lipids, derivatized lipids, and the like.

In some embodiments, the lipid suspension comprises an amphiphilic lipid, a sterol, and a (polyethylene glycol)-lipid. In some examples, the amphiphilic lipid is a phosphatidylcholine lipid. Suitable phosphatidylcholine lipids (PCs) include saturated PCs and unsaturated PCs. Examples of saturated PCs include 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC),1-palmitoyl-2-stearoyl-sn-glycero-3-phosphocholine (PSPC), 1-stearoyl-2-palmitoyl-sn-glycero-3-phosphocholine (SPPC), and 1-stearoyl-2-myristoyl-sn-glycero-3-phosphocholine (SMPC).

Examples of unsaturated PCs include, but are not limited to, 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine, POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC). Lipid extracts, such as egg PC, heart extract, brain extract, liver extract, soy PC, and hydrogenated soy PC (HSPC) can also be used in the methods of the invention.

In some examples, the amphiphilic lipid is selected from the group consisting of hydrogenated soy phosphatidylcholine, 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), 1-stearoyl-2-myristoyl-sn-glycero-3-phosphocholine (SMPC), 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3phosphocholine (OMPC), 1-oleoyl-2-palmitoyl-sn-glycero-3-phosphocholine (OPPC), and 1-oleoyl-2-stearoyl-sn-glycero-3-phosphocholine (OSPC).

The lipid suspensions provided herein will, in some embodiments, consist essentially of PC/cholesterol/PEG-lipid mixtures. In some embodiments, the liposome suspensions will consist essentially of a phosphatidylcholine lipid or mixture of phosphatidylcholine lipids, with a sterol, and a PEG-lipid. In some embodiments, when a single type of phosphatidylcholine lipid is used, it is selected from DOPC, DSPC, HSPC, DPPC, POPC and SOPC.

In some embodiments, the phosphatidylcholine lipid is selected from the group consisting of DPPC, DSPC, HSPC, and mixtures thereof. Any suitable amount of phosphatidylcholine or phosphatidylcholine mixture can be used in the lipid suspension. For example, the amount of phosphatidylcholine or phosphatidylcholine mixture in the lipid suspension can range from about 40 mol % to about 43 mol %, or from about 43 mol % to about 46 mol %, or from about 46 mol % to about 49 mol %, or from about 49 mol % to about 52 mol %, or from about 52 mol % to about 55 mol %, or from about 55 mol % to about 58 mol %, or from about 58 mol % to about 61 mol %, or from about 61 mol % to about 64 mol %, or from about 64 mol % to about 67 mol %, or from about 67 mol % to about 70 mol %. The amount of phosphatidylcholine or phosphatidylcholine mixture in the lipid suspension can range from about 40 mol % to about 70 mol %, or from about 42 mol % to about 68 mol %, or from about 44 mol % to about 66 mol %, or from about 46 mol % to about 64 mol %, or from about 48 mol % to about 62 mol %, or from about 50 mol % to about 60 mol %, or from about 52 mol % to about 58 mol %, or from about 54 mol % to about 56 mol %. In some embodiments, the liposomes contain 50-65 mol % of a phosphatidylcholine lipid or mixture of phosphatidylcholine lipids, or 45-70 mol % of a phosphatidylcholine lipid or mixture of phosphatidylcholine lipids. The liposomes can contain, for example, 50, 51, 52, 53, 54, 55, 56, 57, 58, 59, 60, 61, 62, 63, 64 or 65 mol % phosphatidylcholine. In some embodiments, the lipid suspensions contain, about 56 mol % phosphatidylcholine.

Other suitable phospholipids, generally used in low amounts or in amounts less than the phosphatidylcholine lipids, include phosphatidic acids (PAs), phosphatidylethanolamines (PEs), phosphatidylglycerols (PGs), phosphatidylserine (PSs), and phosphatidylinositol (PIs). Examples of phospholipids include, but are not limited to, 1,2-distearoyl-sn-glycero-3-phosphate (DSPA), dimyristoylphosphatidylglycerol (DMPG), distearoylphosphatidylglycerol (DSPG), dioleoylphosphatidylglycerol (DOPG), dipalmitoylphosphatidylglycerol (DPPG), dimyristoylphosphatidylserine (DMPS), distearoylphosphatidylserine (DSPS), dioleoylphosphatidylserine (DOPS), dipalmitoylphosphatidylserine (DPPS), dioleoylphosphatidylethanolamine (DOPE), palmitoyloleoylphosphatidylcholine (POPC), palmitoyloleoylphosphatidylethanolamine (POPE), dipalmitoylphosphatidylethanolamine (DPPE), dimyristoylphosphoethanolamine (DMPE), distearoylphosphatidylethanolamine (DSPE), 16-O-monomethyl PE, 16-O-dimethyl PE, 18-1-trans PE, 1-stearoyl-2-oleoyl-phosphatidyethanolamine (SOPE), dielaidoylphosphoethanolamine (transDOPE), and cardiolipin.

In some embodiments, phospholipids can include reactive functional groups for further derivatization. Examples of such reactive lipids include, but are not limited to, dioleoylphospha-tidylethanolamine-4-(N-maleimidomethyl)-cyclohexane-1-carboxylate (DOPE-mal) and dipalmitoylphosphatidylethanolamine-N-succinyl (succinyl-PE).

In general, the lipid suspensions contain at least one sterol. In some cases, the sterol is cholesterol or a cholesterol derivative, such as 2,15-dimethyl-14-(1,5-dimethylhexyl) tetracyclo[8.7.0.0$^{2.7}$.0$^{11.15}$]heptacos-7-en-5-ol) or cholesteryl pelargonate. Other sterols, including stigmasterol, campesterol, zymostenol, sitosterol, and pregnenolone, can also be used in the lipid suspension. Any suitable amount of sterol can be used in the lipid suspension. For example, the amount of the sterol or sterol mixture in the lipid suspension can range from about 20 mol % to about 24 mol %, or from about 24 mol % to about 28 mol %, or from about 28 mol % to about 32 mol %, or from about 32 mol % to about 36 mol %, or from about 36 mol % to about 40 mol %, or from about 40 mol % to about 44 mol %, or from about 44 mol % to about 48 mol %, or from about 48 mol % to about 50 mol %. The amount of the sterol or sterol mixture in the lipid suspension can range from about 20 mol % to about 50 mol %, or from about 23 mol % to about 47 mol %, or from about 26 mol % to about 44 mol %, or from about 29 mol % to about 41 mol %, or from about 32 mol % to about 38 mol %, or from about 35 mol % to about 35 mol %, or from about 38 mol % to about 32 mol %, or from about 41 mol % to about 29 mol %, or from about 44 mol % to about 26 mol %, or from about 47 mol % to about 23 mol %, or from about 50 mol % to about 20 mol %. In some embodiments, the liposomes can contain about 20-50 mol % sterol, or about 25-35 mol % sterol. The liposomes can contain, for example, 24, 26, 27, 28, 29, 30, 31, 32, 33, 34, 35, 36, 37, 38, 39, 40, 41, 42, 43, 44, or 45 mol % sterol. In some embodiments, the lipid suspensions contain 30-40 mol % cholesterol. In some embodiments, the liposomes contain 20-30 mol % cholesterol. In some embodiments, the lipid suspensions contain 30 mol % cholesterol. In some embodiments, the lipid suspensions contain 39 mol % cholesterol. Lipid suspensions of the present invention can contain other steroids, characterized by the presence of a fused, tetracyclic gonane ring system. Examples of steroids include, but are not limited to, cholic acid, progesterone, cortisone, aldosterone, testosterone, dehydroepiandrosterone, and estradiol. Synthetic steroids and derivatives thereof are also contemplated for use in the present invention.

In some embodiments, the lipid suspensions also contain a (polyethylene glycol)-lipid. The presence of PEG on the surface of a liposome has been shown to extend blood-circulation time while reducing mononuclear phagocyte system uptake, creating so-called "stealth" liposomes as described in U.S. Pat. Nos. 5,013,556 and 5,827,533, each of which is incorporated herein by reference in its entirety. In some embodiments, the (polyethylene glycol)-lipid is a (polyethylene glycol)-phosphatidylethanolamine. In some embodiments, the liposomes produced by the method have an average diameter of 100 nm and polyethylene glycol brush densities of greater than 25,000 polyethylene glycol chains per liposome, or greater than 50,000 polyethylene glycol chains per liposome, or greater than 100,000 polyethylene glycol chains per liposome, or greater than 200,000 polyethylene glycol chains per liposome, or greater than 250,000 polyethylene glycol chains per liposome. In some embodiments, the liposomes have an average diameter of 50 nm and polyethylene glycol brush densities of greater than 25,000 polyethylene glycol chains per liposome, or greater than 50,000 polyethylene glycol chains per liposome, or greater than >100,000 polyethylene glycol chains per liposome, or greater than 250,000 polyethylene glycol chains per liposome. In some embodiments, the liposomes comprising a sterol in amount of at least 30 mole percent have polyethylene glycol brush densities of >100,000 polyethylene glycol chains per liposome having an average diameter of 100 nm.

The lipid suspensions may include any suitable poly (ethylene glycol)-lipid derivative (PEG-lipid). In some embodiments, the PEG-lipid is a diacyl-phosphatidylethanolamine-N-[methoxy(polyethylene glycol)]. The molecular weight of the poly(ethylene glycol) in the PEG-lipid is generally in the range of from about 500 Daltons (Da) to about 5000 Da. The poly(ethylene glycol) can have a molecular weight of, for example, about 750 Da, about 1000 Da, about 2500 Da, or about 5000 Da, or about 10,000 Da, or any molecular weight within this range. In some embodiments, the PEG-lipid is selected from distearoyl-phosphatidylethanolamine-N-[methoxy(polyethylene glycol)-2500] (DSPE-PEG-2500) and distearoyl-phosphatidylethanolamine-N-[methoxy(polyethylene glycol)-5000] (DSPE-PEG-5000). In some embodiments, the PEG-lipid is DSPE-PEG-2500. In other embodiments, the PEG-lipid is DSPE-PEG-5000.

Any suitable amount of PEG-lipid can be used in the lipid suspension. For example, the amount of the PEG-lipid in the lipid suspension can range from about 1 mol % to about 2 mol %, or from about 2 mol % to about 3 mol %, or from about 3 mol % to about 4 mol %, or from about 4 mol % to about 5 mol %, or from about 5 mol % to about 6 mol %, or from about 6 mol % to about 7 mol %, or from about 7 mol % to about 8 mol %, or from about 8 mol % to about 9 mol %, or from about 9 mol %, to about 10 mol %. The amount of the PEG-lipid in the lipid suspension can range from about 1 mol % to about 10 mol %, or from about 2 mol % to about 9 mol %, or from about 3 mol % to about 8 mol %, or from about 4 mol % to about 7 mol %. In some embodiments the lipid suspensions contain 1-8 mol % of the PEG-lipid. The liposomes can contain, for example 1, 2, 3, 4, 5, 6, 7, or 8 mol % PEG-lipid. In some embodiments, the liposomes contain 2-6 mol % PEG-lipid. In some embodiments, the liposomes contain 3 mol % PEG-lipid. In some embodiments, the liposomes contain 5 mol % DSPE-PEG-2000.

In some examples, the lipid suspensions comprise a sterol in an amount of at least 30 mole percent and further comprise an amphiphilic lipid and a (polyethylene glycol)-lipid. In some embodiments, the sterol is cholesterol or a cholesterol derivative. In some examples, the (polyethylene glycol)-lipid is a (polyethylene glycol)-phosphatidylethanolamine. In some instances, the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amino(polyethylene glycol)-5K.

In some embodiments, the lipid suspension contains from about 50 mol % to about 65 mol % HSPC, from about 35 mol % to about 45 mol % cholesterol, and from about 2 mol % to about 8 mol % DSPE-PEG5K. In some embodiments, the lipid suspension contains from about 50 mol % to about 70 mol % DPPE, from about 30 mol % to about 40 mol % cholesterol, and from about 2 mol % to about 8 mol % DSPE-PEG5K.

In some embodiments, the lipid suspension contains from about 50 mol % to about 70 mol % DPPE, from about 30 mol % to about 40 mol % cholesterol, from about 0.1 mol % to about 0.5 mol % DPPE-Cy5.5, and from about 1.5 mol % to about 8 mol % DSPE-PEG5K. In some embodiments, the lipid suspension contains from about 50 mol % to about 65 mol % HSPC, from about 35 mol % to about 45 mol % cholesterol, from about 0.1 mol % to about 0.5 mol % DPPE-Cy5.5, and from about 1.5 mol % to about 8 mol % DSPE-PEG5K.

In some embodiments, the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amine(polyethylene glycol)-5K. In some embodiments, a 56:39:5 molar ratio of HSPC:cholesterol:DSPE-PEG5K is used. In some embodiments, a 60:35:5 molar ratio of DPPE:cholesterol:DSPE-PEG5K is used. In some embodiments, a 60:35:0.1.4.9 molar ratio of DPPE:cholesterol:DPPE-Cy5.5.DSPE-PEG5K is used. In some embodiments, a 60:53:0.1.4.9 molar ratio of HSPC:cholesterol:DPPE-Cy5.5.DSPE-PEG5K is used.

Further lipids can be included in the lipid suspensions and liposomes including, but not limited to, quanternary amine-based cationic lipids (e.g., 1,2-di-O-octadecenyl-3-trimethylammonium propane (DOTMA), 1,2-dioleoyl-3-trimethylammonium-propane (DOTAP), Dimethyldioctadecylammonium bromide salt (DDAB), and the like), diacylglycerols (e.g., 1,2-dipalmitoyl-sn-glycerol, glycerol distearate, and the like); alkyl phosphates (1,2-dipalmitoyl-sn-glycero-3-phosphomethanol, 1,2-dioleoyl-sn-glycero-3-phosphoethanolamine-N,N-dimethyl, and the like), and 2-((2,3-bis(oleoyloxy)propyl)dimethylammonio)ethyl ethyl phosphate (DOCP).

The methods provided are particularly useful for producing liposomes having an average diameter of less than about 100 nm. The diameter of the liposomes can range, for example, from about 5 nm to about 10 nm, or from about 10 nm to about 20 nm, or from about 20 nm to about 30 nm, or from about 30 nm to about 40 nm, or from about 40 nm to about 50 nm, or from about 50 nm to about 60 nm, or from about 60 nm to about 70 nm, or from about 70 nm to about 80 nm, or from about 80 nm to about 90 nm, or from about 90 nm to about 95 nm. The diameter of the liposomes can range from about 35 nm to about 40 nm, or from about 40 nm to about 45 nm, or from about 45 nm to about 50 nm, or from about 40 nm to about 60 nm, or from about 20 nm to about 80 nm, or from about 10 nm to about 90 nm. The diameter of the liposomes can be about 40, 41, 42, 43, 44, 45, 46, 47, 48, 49, 50, 51, 52, 53, 54, or 55 nm. Liposomes of this size have proven difficult to produce via previously known methods, particularly when a sterol such as cholesterol is incorporated in about 20-40 mol %, or in about 30 mol %, or in greater than 30 mol %.

The methods provided are also particularly useful for producing liposomes having an average diameter that is substantially less than the pore diameter of the filter membranes. Thus, for instance, a 100 nm-pore filter membrane can be used to produce liposomes having a diameter of 50 nm. In some embodiments, the ratio of the average filter pore size to the average liposome diameter is 1.2 or greater, 1.4 or greater, 1.6 or greater, 1.8 or greater, 2.0 or greater, or 3.0 or greater. In some embodiments, the ratio of the average filter pore size to the average liposome diameter is from 1.2 to 3.0, or from 1.6 to 2.0. In some embodiments, the average pore size of the filters is about 100 nm and the average diameter of the liposomes is about 80 nm, about 70 nm, about 60 nm, about 50 nm, or about 45 nm.

The liposome populations produced via the methods described herein have low polydispersities, generally having a polydispersity index that is less than 0.3, less than 0.2, less than 0.15, of less than 0.10, as measured by DLS.

The liposome populations produced via the methods described herein may be unilamellar vesicles which are comprised of a single lipid bilayer and generally have a diameter in the range of about 20 to about 400 nm. Liposomes can also be multilamellar, which generally have a diameter in the range of 1 to 10 μm. In some embodiments, liposomes can include multilamellar vesicles (MLVs; from about 1 μm to about 10 μm in size), large unilamellar vesicles (LUVs; from a few hundred nanometers to about 10 μm in size), and/or small unilamellar vesicles (SUVs; from about 20 nm to about 200 nm in size). In some instances, the liposomes are small unilamellar vesicles.

In some examples, the liposomes are produced when the lipid suspension is passed through the filter assembly more than once. In some embodiments, the average diameter of the liposomes decreases with each additional pass through the filter assembly.

Yield can be used to express the amount of lipids from the lipid suspension that are not lost during filtration. In some embodiments, the lipid suspension is converted to liposomes with a yield of at least about 50% (w/w), at least about 60% (w/w), at least about 70% (w/w), at least about 80% (w/w), or at least about 90% (w/w).

II. LIPOSOMES

A variety of liposomes can be prepared using the methods and systems described herein. In certain embodiments, liposomes that comprise a sterol in amount of at least 30 mole percent, wherein the average diameter of the liposomes is less than 100 nm, are provided.

In some embodiments, liposomes are prepared from a lipid suspension. The lipid suspension is prepared by adding the desired lipids in the desired molar ratios to an aqueous solvent, and then dispersing the lipids in the solvent. The lipid suspension can contain any suitable lipid, including cationic lipids, zwitterionic lipids, neutral lipids, or anionic lipids as described above. Suitable lipids can include fats, waxes, steroids, sterols, cholesterol, fat-soluble vitamins, monoglycerides, diglycerides, phospholipids, sphingolipids, glycolipids, cationic or anionic lipids, derivatized lipids, and the like.

In some embodiments, the liposomes comprise an amphiphilic lipid, a sterol, and a (polyethylene glycol)-lipid. In some examples, the amphiphilic lipid is a phosphatidylcholine lipid. Suitable phosphatidylcholine lipids include saturated PCs and unsaturated PCs. Examples of saturated PCs include 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphastidylcholine; DPPC), 1,2-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), and 1-stearoyl-2-myristoyl-sn-glycero-3-phosphocholine (SMPC).

Examples of unsaturated PCs include, but are not limited to, 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC), and lipid extracts, such as egg PC, heart extract, brain extract, liver extract, soy PC, and hydrogenated soy PC (HSPC) are also useful in the present invention.

In some embodiments, the amphiphilic lipid is selected from the group consisting of hydrogenated soy phosphatidylcholine, 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), 1-stearoyl-2-myristoyl-sn-glycero-3-phosphocholine (SMPC), 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC). Lipid extracts, such as egg PC, heart extract, brain extract, liver extract, soy PC, and hydrogenated soy PC (HSPC).

The liposomes provided herein will, in some embodiments, consist essentially of PC/cholesterol/PEG-lipid mixtures. In some embodiments, the liposomes will consist essentially of a phosphatidylcholine lipid or mixture of phosphatidylcholine lipids, with a sterol, and a PEG-lipid. In some embodiments, when a single type of phosphatidylcholine lipid is used, it is selected from DOPC, DSPC, HSPC, DPPC, POPC and SOPC.

In some embodiments, the phosphatidylcholine lipid is selected from the group consisting of DPPC, DSPC, MSPC, and mixtures thereof. The liposomes can contain any suitable amount of phosphatidylcholine or phosphatidylcholine mixture. For example, the amount of phosphatidylcholine or phosphatidylcholine mixture in the liposomes can range from about 40 mol % to about 43 mol %, or from about 43 mol % to about 46 mol %, or from about 46 mol % to about 49 mol %, or from about 49 mol % to about 52 mol %, or from about 52 mol % to about 55 mol %, or from about 55 mol % to about 58 mol %, or from about 58 mol % to about 61 mol %, or from about 61 mol % to about 64 mol %, or from about 64 mol % to about 67 mol %, or from about 67 mol % to about 70 mol %. The amount of phosphatidylcholine or phosphatidylcholine mixture in the liposomes can range from about 40 mol % to about 70 mol %, or from about 42 mol % to about 68 mol %, or from about 44 mol % to about 66 mol %, or from about 46 mol % to about 64 mol %, or from about 48 mol % to about 62 mol %, or from about 50 mol % to about 60 mol %, or from about 52 mol % to about 58 mol %, or from about 54 mol % to about 56 mol %. In some embodiments, the liposomes contain 50-65 mol % of a phosphatidylcholine lipid or mixture of phosphatidylcholine lipids or 45-70 mol % of a phosphatidylcholine lipid or mixture of phosphatidylcholine lipids. The liposomes can contain, for example, 50, 51, 52, 53, 54, 55, 56, 57, 58, 59, 60, 61, 62, 63, 64 or 65 mol % phosphatidylcholine. In some embodiments, the liposomes contain about 56 mol % phosphatidylcholine.

Other suitable phospholipids, generally used in low amounts or in amounts less than the phosphatidylcholine lipids, include phosphatidic acids (PAs), phosphatidylethanolamines (PEs), phosphatidylglycerols (PGs), phosphatidylserine (PSs), and phosphatidylinositol (PIs). Examples of phospholipids include, but are not limited to, 1,2-distearoyl-sn-glycero-3-phosphate (DSPA), dimyristoylphosphatidylglycerol (DMPG), distearoylphosphatidylglycerol (DSPG), dioleoylphosphaltidylglycerol (DOPG), dipalmitoylphosphatidylglycerol (DPPG), dimyristoylphosphatidylserine (DMPS), distearoylphosphatidylserine (DSPS), dioleoylphosphatidylserine (DOPS), dipalmitoylphosphatidylserine (DPPS), dioleoylphosphatidylethanolamine (DOPE), palmitoyloleoylphosphatidylcholine (POPC), palmitoyloleoylphosphatidylethanolamine (POPE), dipalmitoylphosphatidylethanolamine (DPPE), dimyristoylphosphoethanolamine (DMPE), distearoylphosphatidylethanolamine (DSPE), 16-O-monomethyl PE, 16-O-dimethyl PE, 18-1-trans PE, 1-stearoyl-2-oleoyl-phosphatidyethanolamine (SOPE), dielaidoylphosphoethanolamine (transDOPE), and cardiolipin.

In some embodiments, phospholipids can include reactive functional groups for further derivatization. Examples of such reactive lipids include, but are not limited to, dioleoylphospha-tidylethanolamine-4-(N-maleimidomethyl)-cyclohexane-1-carboxylate (DOPE-mal) and dipalmitoylphosphatidylethanolamine-N-succinyl (succinyl-PE).

In general, the liposomes contain at least one sterol. In some cases, the sterol is cholesterol or a cholesterol derivative, such as 2,15-dimethyl-14-(1,5-dimethylhexyl)tetracyclo[8.7.0.0$^{2.7}$.0$^{11.15}$]heptacos-7-en-5-ol) or cholesteryl pelargonate. Other sterols, including stigmasterol, campesterol, zymostenol, sitosterol, and pregnenolone, can also be included in the liposomes. The liposomes can contain any suitable amount of sterol. For example, the amount of the sterol or sterol mixture in the liposomes can range from about 20 mol % to about 24 mol %, or from shout 24 mol % to about 28 mol %, or from about 28 mol % to about 32 mol %, or from about 32 mol % to about 36 mol %, or from about 36 mol % to about 40 mol %, or from about 40 mol % to about 44 mol %, or from about 44 mol % to about 48 mol %, or from about 48 mol % to about 50 mol %. The amount of the sterol or sterol mixture in the liposomes can range from about 20 mol % to about 50 mol %, or from about 23 mol % to about 47 mol %, or from about 26 mol % to about 44 mol %, or from about 29 mol % to about 41 mol %, or from about 32 mol % to about 38 mol %, or from about 35 mol % to about 35 mol %, or from about 38 mol % to about 32 mol %, or from about 41 mol % to about 29 mol %, or from about 44 mol % to about 26 mol %, or from about 47 mol % to about 23 mol %, or from about 50 mol % to about 20 mol %. In some embodiments, the liposomes can contain about 20-50 mol % sterol, or about 25-35 mol % sterol. The liposomes can contain, for example, 24, 26, 27, 28, 29, 30, 31, 32, 33, 34, 35, 36, 37, 38, 39, 40, 41, 42, 43, 44, or 45 mol % sterol. In some embodiments, the liposomes contain 30-40 mol % cholesterol. In some embodiments, the liposomes contain 20-30 mol % cholesterol. In some embodiments, the liposomes contain 30 mol % cholesterol. In some embodiments, the liposomes contain 39 mol % cholesterol. Liposomes of the present invention can contain other steroids, characterized by the presence of a fused, tetracyclic gonane ring system. Examples of steroids include, but are not limited to, cholic acid, progesterone, cortisone, aldosterone, testosterone, dehydroepiandrosterone, and estradiol. Synthetic steroids and derivatives thereof are also contemplated for use in the present invention.

In some embodiments, the liposomes also contain a (polyethylene glycol)-lipid. The presence of PEG on the surface of a liposome has been shown to extend blood-circulation time while reducing mononuclear phagocyte system uptake, creating so-called "stealth" liposomes as described in U.S. Pat. Nos. 5,013,556 and 5,827,533, each of which is hereby incorporated by reference in its entirety. In some embodiments, the (polyethylene glycol)-lipid is a (polyethylene glycol)-phosphatidylethanolamine.

The liposomes may include any suitable poly(ethylene glycol)-lipid derivative (PEG-lipid). In some embodiments, the PEG-lipid is a diacyl-phosphatidylethanolamine-N-[methoxy(polyethylene glycol)]. The molecular weight of the poly(ethylene glycol) in the PEG-lipid is generally in the range of from about 500 Daltons (Da) to about 5000 Da. The poly(ethylene glycol) can have a molecular weight of, for example, about 750 Da, about 1000 Da, about 2500 Da, or about 5000 Da, or about 10,000 Da, or any molecular weight within this range. In some embodiments, the PEG-lipid is selected from distearoyl-phosphatidylethanolamine-N-[methoxy(polyethylene glycol)-2500] (DSPE-PEG-2500) and distearoyl-phosphatidylethanolamine-N-[methoxy(polyethylene glycol)-5000] (DSPE-PEG-5000). In some embodiments, the PEG-lipid is DSPE-PEG-2500. In other embodiments, the PEG-lipid is DSPE-PEG-5000.

The liposomes may contain any suitable amount of PEG-lipid. For example, the amount of the PEG-lipid in the liposomes can range from about 1 mol % to about 2 mol %, or from about 2 mol % to about 3 mol %, or from about 3 mol % to about 4 mol %, or from about 4 mol % to about 5 mol %, or from about 5 mol % to about 6 mol %, or from about 6 mol % to about 7 mol %, or from about 7 mol % to about 8 mol %, or from about 8 mol % to about 9 mol %, or from about 9 mol % to about 10 mol %. The amount of the PEG-lipid in the liposomes can range from about 1 mol % to about 10 mol %, or from about 2 mol % to about 9 mol %, or from about 3 mol % to about 8 mol %, or from about 4 mol %, to about 7 mol %. In some embodiments, the liposomes contain 1-8 mol % of the PEG-lipid. The liposomes can contain, for example, 1, 2, 3, 4, 5, 6, 7, or 8 mol % PEG-lipid. In some embodiments, the liposomes contain 2-6 mol % PEG-lipid. In some embodiments, the liposomes contain 3 mol % PEG-lipid. In some embodiments, the liposomes contain 5 mol % DSPE-PEG-2000.

In some embodiments, the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amine(polyethylene glycol)-5K. In some embodiments, a 56:39:5 molar ratio of HSPC:cholesterol:DSPE-PEG5K is used. In other embodiments, a 60:35:5 molar ratio of DPPE:cholesterol:DSPE-PEG5K is used. In addition, a 60:35:0.1.4.9 molar ratio of DPPE cholesterol:DPPE-Cy5.5:DSPE-PEG5K is used. In some embodiments, a 60:35:0.1.4.9 molar ratio of HSPC:cholesterol:DPPE-Cy5.5: DSPE-PEG5K is used.

In some embodiments, the liposomes contain from about 50 mol % to about 65 mol % HSPC, from about 35 mol % to about 45 mol % cholesterol, and from about 2 mol % to about 8 mol % DSPE-PEG5K. In some embodiments, the liposomes contain from about 50 mol % to about 70 mol % DPPE, from about 30 mol % to about 40 mol % cholesterol, and from about 2 mol % to about 8 mol % DSPE-PEG5K.

In some embodiments, the liposomes contain from about 50 mol % to about 70 mol % DPPE, from about 30 mol % to about 40 mol % cholesterol, from about 0.1 mol % to about 0.5 mol % DPPE-Cy5.5, and from about 1.5 mol % to about 8 mol % DSPE-PEG5K. In some embodiments, the liposomes contain from about 50 mol % to about 65 mol % HSPC, from about 35 mol % to about 45 mol % cholesterol, from about 0.1 mol % to about 0.5 mol % DPPE-Cy5.5, and from about 1.5 mol % to about 8 mol % DSPE-PEG5K.

In some examples, the liposomes comprising a sterol in an amount of at least 30 mole percent further comprise an amphiphilic lipid and a (polyethylene glycol)-lipid. In some embodiments, the sterol is cholesterol or a cholesterol derivative. In some examples, the (polyethylene glycol)-lipid is a (polyethylene glycol)-phosphatidylethanolamine. In some instances, the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amino(polyethylene glycol)-5K.

In some embodiments, the liposomes have an average diameter of 100 nm and polyethylene glycol brush densities of >25,000 polyethylene glycol chains per liposome, >50,000 polyethylene glycol chains per liposome, >100,000 polyethylene glycol chains per liposome, >200,000 polyethylene glycol chains per liposome, or >250,000 polyethylene glycol chains per liposome.

In some embodiments, the liposomes have an average diameter of 50 nm and polyethylene glycol brush densities of >25 polyethylene glycol chains per liposome, >50 polyethylene glycol chains per liposome, >100 polyethylene glycol chains per liposome, or >250 polyethylene glycol chains per liposome. In some embodiments, the liposomes comprising a sterol in amount of at least 30 mole percent have polyethylene glycol brush densities of >100,000 polyethylene glycol chains per liposome having an average diameter of 100 nm.

The liposomes may be unilamellar vesicles which are comprised of a single lipid bilayer and generally have a diameter in the range of about 20 to about 400 nm. Liposomes can also be multilamellar, which generally have a diameter in the range of 1 to 10 µm. In some embodiments, liposomes can include multilamellar vesicles (MLVs; from about 1 µm to about 10 µm in size), large unilamellar vesicles (LUVs; from a few hundred nanometers to about 10 µm in size), and small unilamellar vesicles (SUVs; from about 20 nm to about 200 nm in size). In some instances, the liposomes are small unilamellar vesicles.

In some embodiments, small liposomes (e.g., diameter of 100 nm or less) contain a 20-40 mol % sterol or sterol derivative. In some instances, liposomes comprising cholesterol in amount of at least 30 mole percent have an average diameter of less than about 100 nm. In some cases, liposomes comprising cholesterol in amount of at least 30 mole percent have an average diameter of less than about 75 nm. In other cases, liposomes comprising cholesterol in amount of at least 30 mole percent have an average diameter of less than about 55 nm. In some instances, liposomes comprising cholesterol in amount of at least 30 mole percent have an average diameter of less than about 50 nm.

In some embodiments, liposomes comprising cholesterol in amount of at least 30 mole percent have a diameter that is the diameter determined by the thermodynamic lower limit of the lipid composition. One of skill in the art will appreciate that the thermodynamic lower limit of the liposome diameter will depend on a number of conditions, including pH, ionic strength, temperature, and type of lipid, among other factors. In some instances, liposomes comprising cholesterol in amount of at least 30 mole percent have an average diameter of about 45 nm. In some instances, the liposomes are small unilamellar vesicles.

It is desirable to produce liposomes having the same molar ratio of component lipids as the lipid suspension from which the liposomes are formed. In other words, it is undesirable for the liposome production method to result in a disproportionate loss of any component lipid. As evidenced below in FIG. 52x12B, the methods of the invention in some embodiments produce liposomes wherein the lipid content of the lipid suspension is substantially identical to the lipid content of the liposomes.

The liposome populations described herein have low polydispersities, generally having a polydispersity index that is less than 0.3, less than 0.2, less than 0.15, or less than 0.10, as measured by DLS. In some cases, the liposomes comprising a sterol in amount of at least 30 mole percent have a polydispersity index of 0.20 or less.

Yield can be used to express the amount of lipids from the lipid suspension that are not lost during filtration. In some embodiments, the lipid suspension is converted to liposomes with a yield of at least about 50%, at least about 60%, at least about 70%, at least about 80%, or at least about 90%.

III. SYSTEMS

Also disclosed are systems for preparing liposomes. Any of the liposomes described in the Liposomes section above may be produced using the systems disclosed herein. Further, any system component described in the Methods or Liposomes section above, such as housings, filters, syringes, syringe filters, orifices, etc. can be used in the systems provided.

In certain embodiments, a system for producing liposomes from a lipid suspension comprises a filter assembly. In some embodiments, the filter assembly comprises two or more filters disposed in series with an orifice disposed between each pair of adjacent filters. In some cases, the filters are aligned such that their faces partially or completely overlap in the field of fluid flow. In some embodiments, the filters are substantially parallel. In some embodiments, the filters are aligned in a column.

In some instances, the system further comprises a filter housing having an inlet and an outlet, wherein the filter assembly is disposed inside the filter housing. In some instances, the filter assembly fits within the filter housing in such a manner that a fluid flowing through the filter housing may not bypass the filters. In some instances, the filter assembly fits within the filter housing in such a manner that a fluid flowing through the filter housing must pass through the filter pores.

In some cases, the system further comprises a component to push, pull, or otherwise move a lipid suspension through the filter assembly. The component can be a plunger, a pump, a vacuum, a gravity feed, or any other known component for moving a fluid through a system.

A flow rate is the volume of fluid that flows through the system per unit time. In some examples, the system has a flow rate of 1 mL/minute or greater, 10 mL/minute or greater, 20 mL/minute or greater, 30 mL/minute or greater, 50 mL/minute or greater, 100 m/min or greater, 1 L/min or greater, 10 L/min or greater, 100 L/min or greater, or 1000 L/min or greater.

The systems disclosed herein allow for the controlled production of liposomes of decreasing diameter as a result of increasing the number of filters in series in the filter assembly, and also as a result of increasing the number of passes through the filter assembly. In some cases, the average diameter of the liposomes decreases with each additional pass through the filter assembly.

In some cases, each filter membrane has a thickness of 1 micron or greater, 2 microns or greater, 3 microns or greater, 5 microns or greater, 50 microns or greater, or 500 microns or greater.

In some embodiments, all filters in the filter assembly have the same diameter. In other embodiments, the filters have different diameters. The filters may be arranged according to increasing diameter, according to decreasing diameters, or randomly with respect to diameter.

Some previously-known systems for the production of liposomes require that the entire filter assembly be heated. In contrast, in some embodiments, the filters and filter housing are at ambient temperature. This ambient temperature can be room temperature (about 20-25° C.) One of skill in the art will appreciate that slight variations in the temperature of the filters and/or filter housing may occur due to heat transfer from lipid suspension to the system. In general, the system does not require a continuous supply of heat, or a supply of heat directly to the filter assembly.

The systems of the present invention are scalable. In some embodiments, the system has a static volume of 1-1000 microliters. In some embodiments, the system has a static volume of 1-1000 milliliters. In some embodiments, the system has a static volume of 1-1000 liters.

A system 110 of the invention is shown in FIG. 1. Two filters 130 are connected in series, with an orifice 140 disposed between. For the system depicted in FIG. 1, the diameter of orifice 140 is less than the diameter of filters 130. A lipid suspension 120 is filtered. A syringe 150 is optionally used as the filter assembly inlet. Optionally, a syringe plunger may be used to move the lipid suspension 120 through the system.

Figure 2:
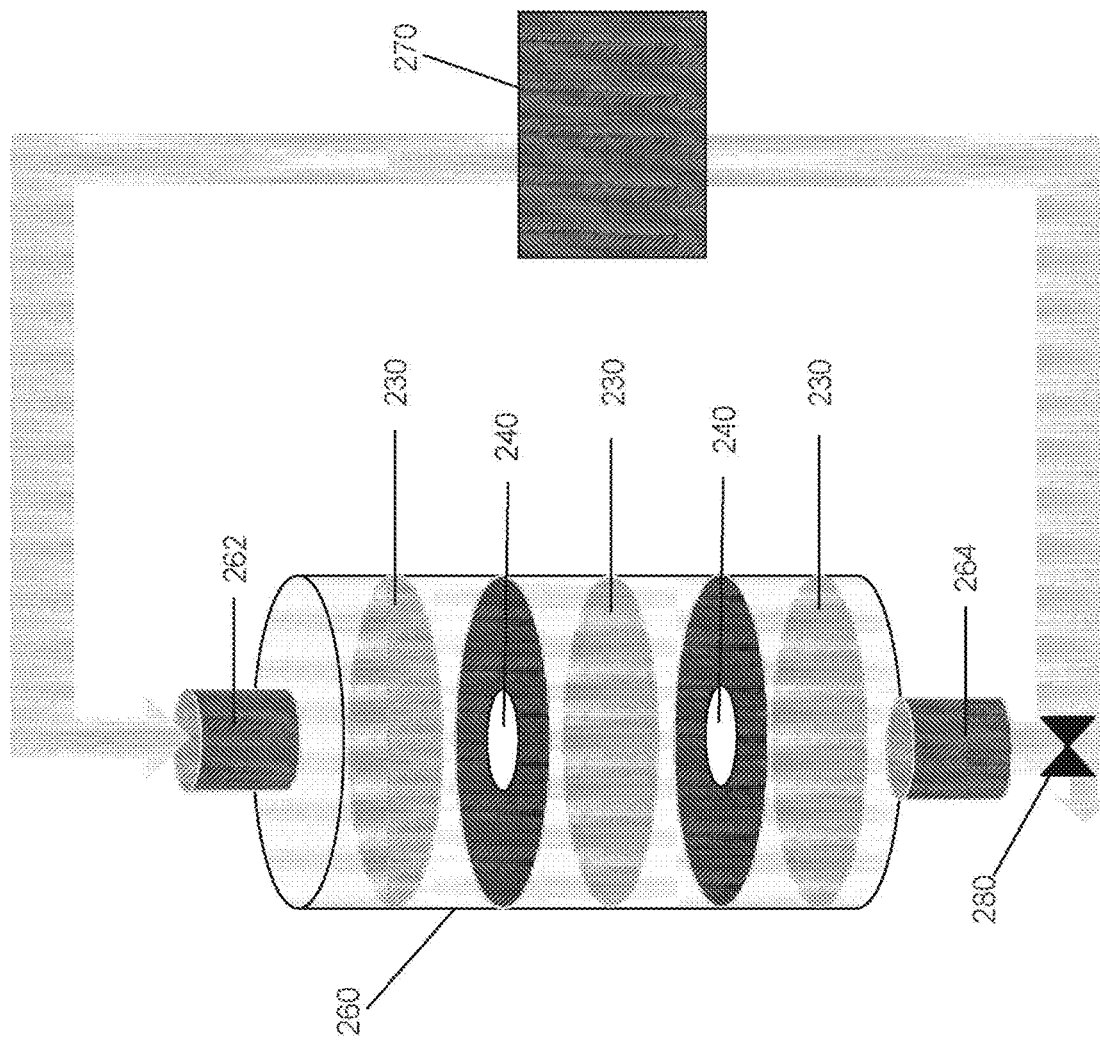
FIG. 2 depicts another system of the invention.

Another system 210 of the invention is shown schematically in FIG. 2. Three filters 230 are connected in series, with an orifice 240 disposed between each two adjacent filters. For the system in FIG. 2, the diameter of orifices 240 is less than the diameter of filters 230. The filter housing 260 comprises an inlet 262 and an outlet 264. The lipid suspension is moved through the filter housing by a component 270, which can be a pump. The lipid suspension may be recirculated through the system or may be removed from the system via valve 280.

IV. EXAMPLES

Example 1. Comparison of Liposome Preparation Via Serial Filtration Methods vs. Extrusion Methods A 56:39:5 molar ratio of HSPC/Cholesterol/DSPE-PEG5K lipid suspension was prepared by adding 12 mg of HSPC ((L-α-phosphatidylcholine, hydrogenated (Soy), Avanti Polar Lipids), 4 milligrams of cholesterol (Sigma-Aldrich), and 8 milligram of DSPE-PEG5K (1,2-distearoyl-sn-glycero-3-phosphoethanolamine-N-[(polyethylene glycol)-5000],) to a 2:1 mixture of chloroform:methanol and dissolving. A thin film of these materials was generated by rotary evaporation at 40° C. at 120 mbar. This film was desiccated overnight until completely dry. Hydration of the lipid film was conducted at 65° C. under sonication in 5 mL of 10 mM HEPES buffer (pH 7.4) for 1 h.

1 mL aliquots of the resulting lipid suspension were filtered through four syringe filters (100 nm pore size, 32 mm diameter, Supor filter, available from Pall Corporation) connected in series, or through a lipid extruder (available from Avanti Polar Lipids. Inc., Alabaster, AL) fitted with four stacked 100 nm membranes or four stacked 50 nm membranes (available from Avanti Polar Lipids). In each case, the suspension was filtered three times through the syringe filters or through the membranes. The diameter and polydispersity index of the resulting Example 1 liposomes are shown below in Table 1.

One pass through 4 filters with orifices disposed between the filters resulting in liposomes having an average diameter of 60.49 nm and a polydispersity of 0.084 (Table 1, Example 1), whereas comparative liposomes produced the filtering through four 100-nm membrane filters stacked with no intervening orifices yielded liposomes with an average diameter of 88.25 nm and a polydispersity of 0.150 (Table 1, Comparative Example 1). Similarly, comparative liposomes produced the filtering through four 50-nm membrane filters stacked with no intervening orifices yielded liposomes with an average diameter of 82.03 nm and a polydispersity of 0.131 (Table 1, Comparative Example 2).

TABLE 1

|  | Method | Filter pore size (nm) | Liposome size (nm) | PDI |
|---|---|---|---|---|
| Example 1 | Serial filtration | 100 | 60.49 | 0.084 |
| Comparative Example 1 | Extrusion | 100 | 88.25 | 0.152 |
| Comparative Example 2 | Extrusion | 50 | 82.03 | 0.131 |

Example 2. Serial Filtration with Increasing Number of Filters

Using the same lipid suspension as prepared in Example 1, 1 mL aliquots were passed through 1, 2 or 4 syringe filters (100 nm pore size, 32 mm diameter, Supor filter, available from Pall Corporation) connected in series as described in Table 2. Smaller particle size is achieved by one pass through 4 filters in series (Table 2, Example 2.3, 70.62 nm) than by four passes through an individual filter (Table 2, Example 2.1, 86.89 nm), even though each lipid suspension passed through 4 filters. Further, a lower polydispersity index was achieved with filters in series.

TABLE 2

|  | Number of filters in series | Number of passes | Liposome size (nm) | PDI |
|---|---|---|---|---|
| Example 2.1 | 1 | 4 | 86.89 | 0.194 |
| Example 2.2 | 2 | 2 | 83.39 | 0.181 |
| Example 2.3 | 4 | 1 | 70.62 | 0.137 |

Figure 3:
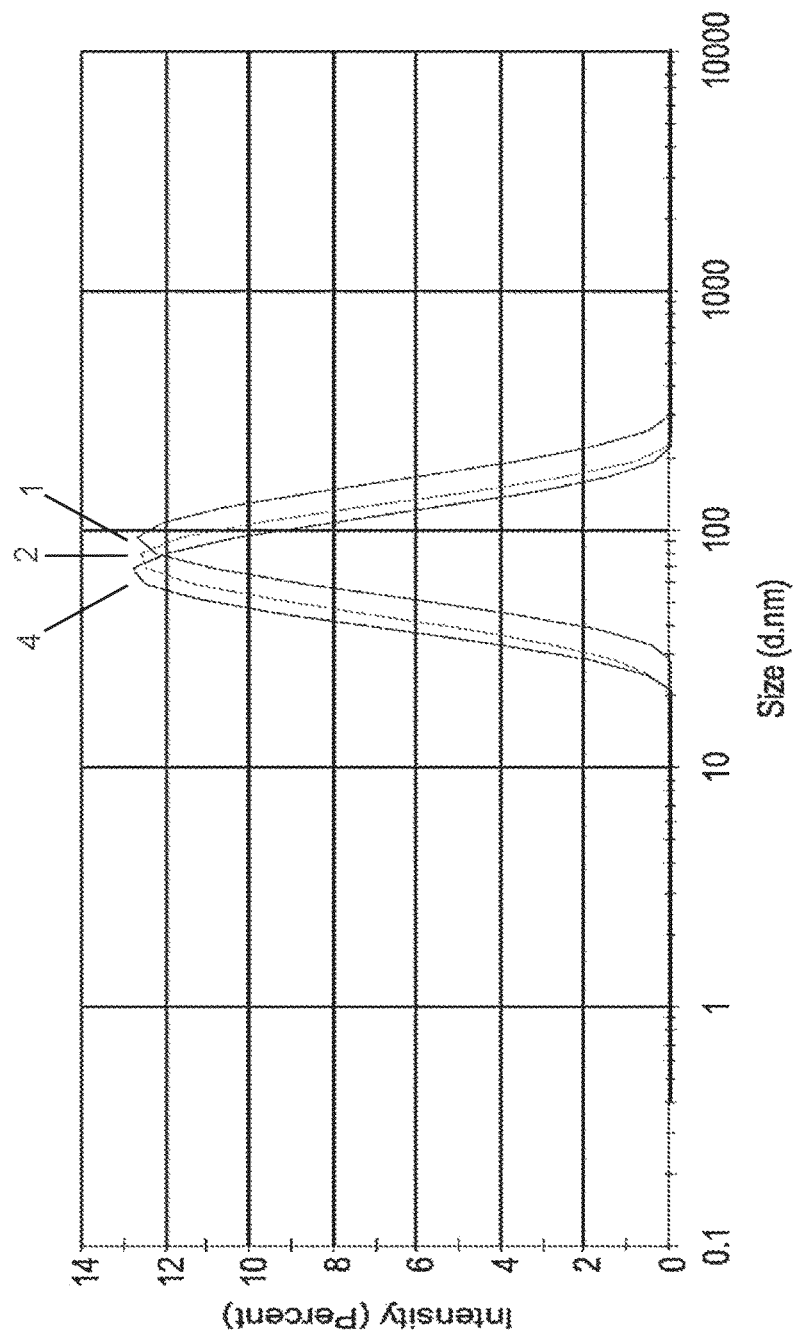
FIG. 3 depicts average particle size and polydispersity of liposomes filtered through 1, 2, or 4 filters (shown as curves labeled 1, 2, and 4, respectively) in series as determined by dynamic light scattering (DLS).

FIG. 3 depicts average particle size and polydispersity of liposomes filtered through 1, 2, or 4 filters in series as determined by DLS.

Example 3. Reproducible Preparation of Monodisperse Liposomes

Figure 4:
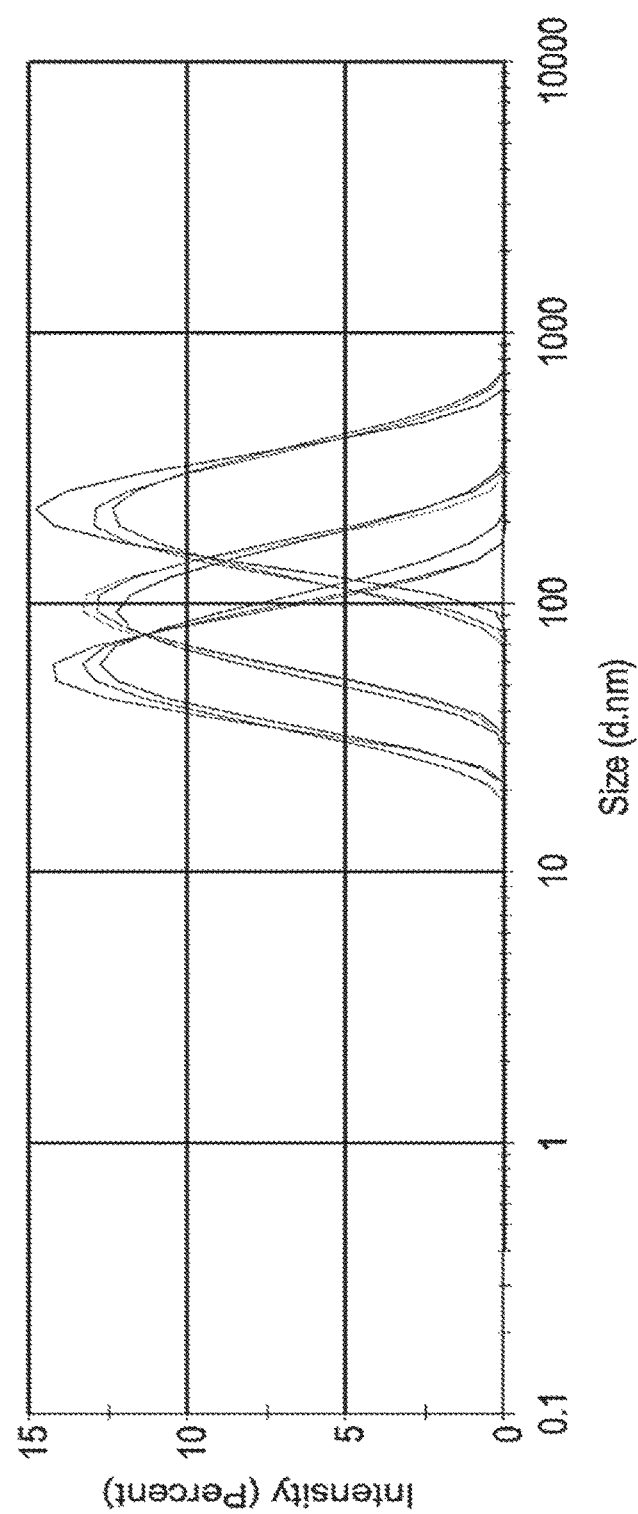
FIG. 4 depicts the reproducible preparation of populations of ~50 nm, ~100 nm, and ~200 nm diameter liposomes, as determined by DLS.

FIG. 4 depicts reproducible preparation of ~50 nm, ~100 nm, and ~200 nm liposomes, as determined by DLS.

Preparation of 200 nm Liposomes

A lipid film containing DPPE:Chol:DPPE-Cy5.5:DSPE-PEG5000 in a molar ratio of 60:35:0.1.4.9 was prepared per the method of Example 1 was hydrated at 69° C. without sonication for 1 h, and then was filtered through one syringe filter (450 nm pore size, 32 mm diameter, Supor filter, available from Pall Corporation)) three times. The resulting the lipid solution was heated in the heated water bath for 5 minutes, and then filtered through one syringe filter (200 nm pore size, 32 mm diameter, Supor filter, available from Pall Corporation)) three times.

Preparation of 100 nm Liposomes

A lipid film containing DPPE:Chol:DPPE-Cy5.5:DSPE-PEG5000 in a molar ratio of 60:35:0.1.4.9 was prepared per the method of Example 1 was hydrated at 69° C. without sonication for 1 h, and then was filtered through one syringe filter (100 nm pore size, 32 mm diameter, Supor filter, available from Pall Corporation) three times.

Preparation of 50 nm Liposomes

Syringe filter stacks were prepared by connecting the syringe filters having 32 mm diameter, available from Pall Corporation as in series as follows:

TABLE 2

| Identifier of Filter Assembly | Number of filters in series | Pore Size | Filter diameter | Quantity |
|---|---|---|---|---|
| "Stack 1" | 3 | 200 nm | 32 mm | 2 |
| "Stack 2" | 3 | 100 nm | 32 mm | 3 |

Each filter stack was pretreated by passing a PBS solution through the stack to pre-wet the membranes. The solution was then removed by passing a stream of air through the filter stack. A lipid solution containing DPPE:Chol:DPPE-Cy5.5:DSPE-PEG5000 in a molar ratio of 60:35:0.1.4.9 was prepared per the method of Example 1, and was sonicated. While the lipid solution was still hot (>63° C.), it was filtered through a Stack 1 filter assembly followed by passing a stream of air through the stack. The resulting suspension was immediately passed through a second Stack 1 filter assembly, followed by passing a stream of air through the stack.

The resulting suspension was sonicated with heat (69° C.) for 5 minutes, and then was filtered through a Stack 2 filter assembly followed by passing a stream of air through the stack. The resulting suspension was sonicated with heat (69° C.) for 5 minutes, and then was filtered through the second Stack 2 filter assembly followed by passing a stream of air through the stack. The resulting suspension was sonicated with heat (69° C.) for 5 minutes, and then was filtered through the third Stack 2 filter assembly followed by passing a stream of air through the stack.

Example 4. Linear Control of PEG Content

Lipid Suspension Preparation. A series of 12 mg:4 mg:0.1 mg:8 mg DPPE:Cholesterol:DPPE-Cy5.5:DSPE-PEG5000 lipid suspensions containing 1.5, 2.5, and 5 mole percent PEG5K, and a lipid suspension containing 5% PEG2000 were prepared.

Figure 6:
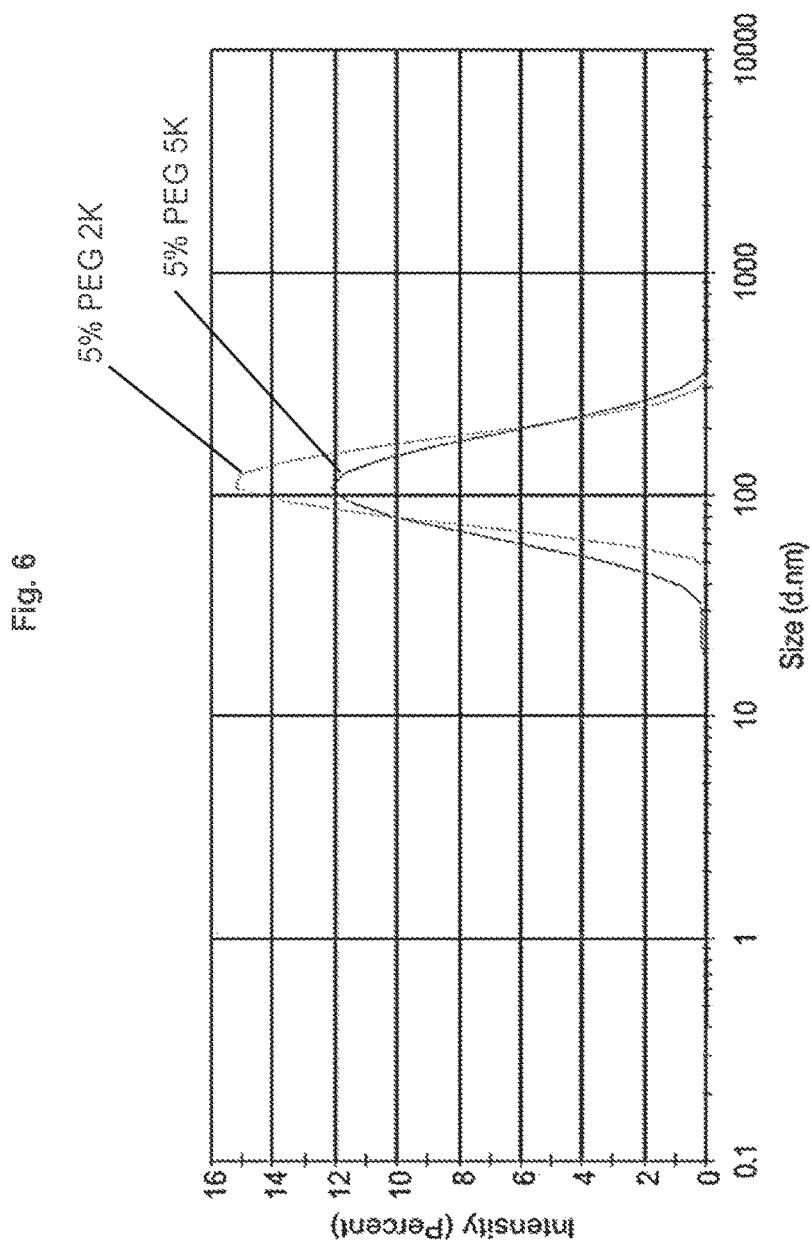
FIG. 6 shows that changing the PEG length (2000 g/mol vs. 5000 g/mol) does not change the particle size of liposomes, as determined by DLS.

1 mL aliquots of the resulting lipid suspensions were filtered as described in Example 3. The PEG loading did not affect the particle size, as shown in FIG. 5A. Linear control of PEG loading (at 1.5%, 2.5%, and 5%) was demonstrated by $^1$H NMR, as shown in FIG. 5B. Further, the PEG lengths of 2000 and 5000 were incorporated at 5 mol % without affecting particle size, as shown in FIG. 6. Determination by NMR was carried out by integration of the peaks at 3.6 ppm and 0.6 ppm. Results show a similar molar incorporation ratio of PEG relative to the cholesterol content for the given lipid content.

Example 5. Storage Stability

The liposomes of Example 4 demonstrated storage stability in Phosphate Buffer Saline (1×) at 4° C. for at least seven days, as shown in Table 3 (PEG2K=PEG2000, or 2000 g/mol; PEG5K=PEG5000, or 5000 g/mol).

TABLE 4

|  | Formulation | Size on Day 0 (nm), PDI | Size on Day 7 (nm), PDI |
| --- | --- | --- | --- |
| Example 5.1 | 5% PEG 2K | 63, 0.106 | 58, 0.119 |
| Example 5.2 | 1.5% PEG 5K | 76, 0.105 | 78, 0.113 |
| Example 5.3 | 2.5% PEG 5K | 72, 0.165 | 70, 0.159 |
| Example 5.4 | 5% PEG 5K | 77, 0.113 | 74, 0.119 |

Example 6. Benefit of Additional Filters in Series

Figure 7:
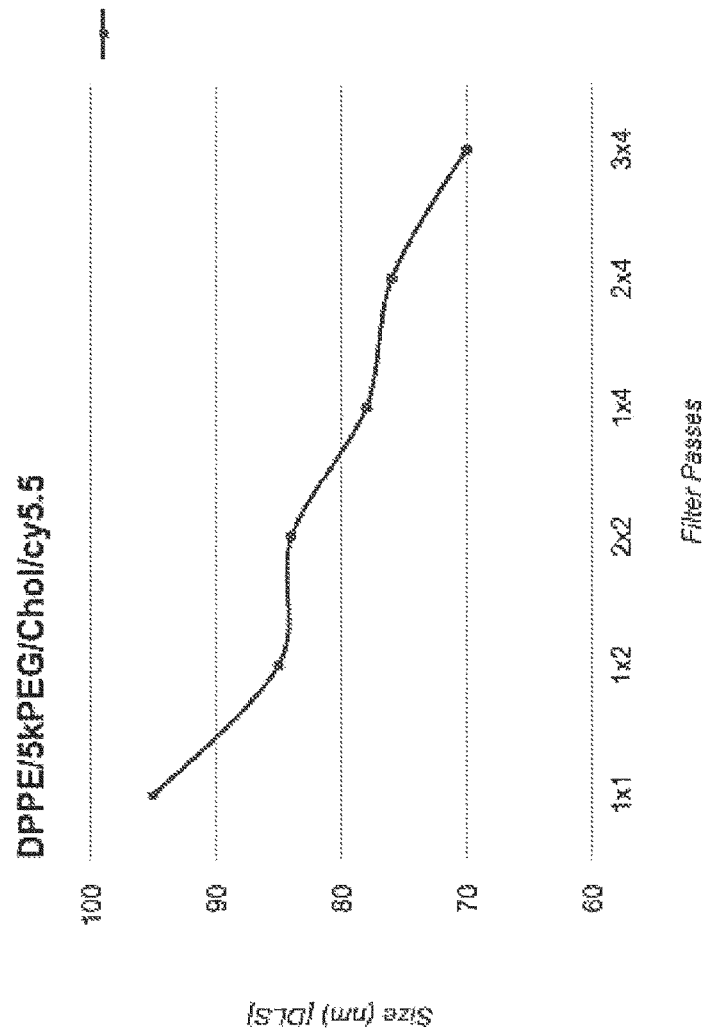
FIG. 7 shows that average liposome particle size decreases with increasing number of filters in series, and with increasing number of passes through those filters, as determined by DLS. The x-axis values indicate the number of passes and the number of filters in series (e.g., 1×1), respectively.

An HSPE:Cholesterol:DPPE-Cy5.5:DSPE-PEG5000 (12 mg:4 mg:0.1 mg:8 mg) lipid suspension was prepared. 1 mL aliquots were passed through 1, 2, or 4 syringe filters (100 nm, 32 mm diameter, Supor filter, available from Pall Corporation) connected in series, for a predetermined number of passes as described in Table 5. Liposome particle size and polydispersity resulting from the filtrations describe in Table 5 are shown in FIG. 7, which demonstrates that progressively smaller liposomes may be produced by increasing the number of filters in series. Further, liposomes produced by 1×4 filtration are smaller that liposomes produced by 2×2 filtration, even though the lipid suspension passed through four filters in each instance. Further still, repeat passes through four filters in series further reduces the size of the liposomes (see 1×4, 2×4, and 3×4). In all cases, the lipid suspensions contained 12 mg of HSPC and 4 mg of cholesterol.

TABLE 5

|  |  | Filtration method | Liposome size(nm), PDI |
| --- | --- | --- | --- |
| Example 6.1 | 1 × 1 | Single pass through one filter | 95, 0.19 |
| Example 6.2 | 1 × 2 | Single pass through two filters in series | 85, 0.17 |
| Example 6.3 | 2 × 2 | Two passes through two filters in series | 84, 0.17 |
| Example 6.4 | 1 × 4 | Single pass through four filters in series | 78, 0.13 |
| Example 6.5 | 2 × 4 | Two passes through four filters in series | 76, 0.17 |
| Example 6.6 | 3 × 4 | Three passes through four filters in series | 70, 0.17 |

Example 7. Control of Liposome Diameter with Number of Passes

The lipid suspension of Example 6 was prepared, and 1 mL aliquots were passed through two syringe filters (100 nm, 32 mm diameter, Supor filter, available from Pall Corporation) connected in series, for an even number of passes from 2-20, as shown in Table 6. Excellent control of liposome particle size was achieved, with diameter decreasing with additional passes until a size plateau was observed at 20 passes, as shown in FIG. 8.

TABLE 6

|  | Passes | Diameter (nm), PDI |
| --- | --- | --- |
| Example 7.1 | 2 | 94.25, 0.18 |
| Example 7.2 | 4 | 83.39, 0.16 |
| Example 7.3 | 6 | 78.93, 0.15 |
| Example 7.4 | 8 | 74.93, 0.16 |
| Example 7.5 | 10 | 69.1, 0.12 |
| Example 7.6 | 12 | 60.67, 0.15 |
| Example 7.7 | 14 | 56.69, 0.19 |
| Example 7.8 | 16 | 64.62, 0.17 |
| Example 7.9 | 18 | 54.24, 0.17 |
| Example 7.10 | 20 | 55,45450.16 |

V. EXEMPLARY EMBODIMENTS

Exemplary embodiments provided in accordance with the presently disclosed subject matter include, but are not limited to, the claims and the following embodiments:

1. A method of producing liposomes, comprising the steps of:
   providing a lipid suspension comprising one or more component lipids;
   heating the lipid suspension to a temperature which is above the phase transition temperature of the component lipids; and
   passing the heated lipid suspension through a filter assembly, wherein the filter assembly comprises two or more filters connected in series, wherein an orifice is disposed between adjacent filters, thereby producing the liposomes.
2. The method of embodiment 1, wherein the diameter of each orifice disposed between adjacent filters is less than or equal to about 70% of the diameter of the filters adjacent to the orifice.
3. The method of embodiment 1 or embodiment 2, wherein the filters comprise alumina-based membranes, polycarbonate-based membranes, polyether sulfone-based membranes, or a combination thereof.

4. The method of any one of the preceding embodiments, wherein the average diameter of the liposomes is less than about 100 nm.
5. The method of any one of the preceding embodiments, wherein the ratio of the average filter pore size to the average liposome diameter is 1.6 or greater.
6. The method of embodiment 5, wherein the average pore size of the filters is about 100 nm and the average diameter of the liposomes is about 50 nm.
7. The method of any one of the preceding embodiments, wherein the pressure in the filter assembly is less than 100 psi.
8. The method of any one of the preceding embodiments, wherein the average filter pore size is about 100 nm.
9. The method of any one of the preceding embodiments, wherein the filter assembly comprises two filters connected in series.
10. The method of any one of embodiments 1-8, wherein the filter assembly comprises three filters connected in series.
11. The method of any one of embodiments 1-8, wherein the filter assembly comprises four filters connected in series.
12. The method of any one of the preceding embodiments, wherein the filters are syringe filters.
13. The method of any one of the preceding embodiments, wherein the liposomes are small unilamellar vesicles.
14. The method of any one of the preceding embodiments, wherein the liposomes have a polydispersity index of 0.20 or less.
15. The method of any one of the preceding embodiments, wherein the lipid suspension comprises an amphiphilic lipid, a sterol, and a (polyethylene glycol)-lipid.
16. The method of embodiment 15, wherein the amphiphilic lipid is selected from the group consisting of hydrogenated soy phosphatidylcholine, 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), 1-stearoyl-2-myristoyl-sn-glycero-3-phosphocholine (SMPC), 1,2-dimyristoleoyl-sn-glycero-3-phosphocholine, 1,2-dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC).

17. The method of embodiment 15 or embodiment 16, wherein the sterol is cholesterol of a cholesterol derivative.
18. The method of any one of embodiments 15-17, wherein the (polyethylene glycol)-lipid is a (polyethylene glycol)-phosphatidylethanolamine.
19. The method of any one of embodiments 15-18, wherein the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amino(polyethylene glycol)-5K.
20. The method of any one of the preceding embodiments, wherein the liposomes have polyethylene glycol brush densities of >100,000 polyethylene glycol chains per liposome having an average diameter of 100 nm.
21. The method of any one of the preceding embodiments, wherein the liposomes comprise cholesterol in amount of at least 30 mole percent.
22. The method of any one of the preceding embodiments, wherein the average diameter of the liposomes is less than about 75 nm.
23. The method of any one of the preceding embodiments, wherein the lipid content of the lipid suspension is substantially identical to the lipid content of the liposomes.
24. The method of any one of the preceding embodiments, wherein the lipid suspension is passed through the filter assembly more than once.
25. The method of any one of the preceding embodiments, wherein the average diameter of the liposomes decreases with each additional pass through the filter assembly.
26. The method of any one of the preceding embodiments, wherein the lipid suspension is converted to liposomes with a yield of at least about 70% (w/w).
27. A system for producing liposomes from a lipid suspension, comprising a filter assembly comprising two or more filters disposed in series and an orifice disposed between each pair of adjacent filters.
28. The system of embodiment 27, further comprising a filter housing having an inlet and an outlet, wherein the filter assembly is disposed inside the filter housing.
29. The system of embodiment 27 or 28, further comprising a component to move a lipid suspension through the filter assembly.
30. The system of any one of embodiments 27-31, wherein the system has a flow rate of 30 mL/minute or greater.
31. The system of any one of embodiments 27-30, wherein the filters comprise alumina-based membranes, polycarbonate-based membranes, polyether sulfone-based membranes, or a combination thereof.
32. The system of any one of embodiments 27-31, wherein the filters have a thickness of 2 microns or greater.
33. The system of any one of embodiments 27-32, wherein the filters have the same diameter.
34. The system of any one of embodiments 27-33, wherein the diameter of each orifice disposed between adjacent filters is less than or equal to about 70% of the diameter of the filters adjacent to the orifice.
35. The system of any one of embodiments 27-34, wherein the filters and filter housing are at ambient temperature during operation of the system.

36. The system of any one of embodiments 27-35, wherein the system has a static volume of 1-1000 microliters.
37. The system of any one of embodiments 27-36, wherein the system has a static volume of 1-1000 milliliters.
38. The system of any one of embodiments 27-36, wherein the system has a static volume of 1-1000 liters.
39. Liposomes prepared according to the method of any one of embodiments 1-26.
40. Liposomes prepared by a passing a lipid suspension through the system of any one of embodiments 27-38.
41. The liposomes of embodiment 39 or 40, wherein the ratio of the average filter pore size to the average diameter of the liposomes is 1.6 or greater.
42. The liposomes of any one of embodiments 39-41, wherein the average filter pore size is about 100 nm and the average diameter of the liposomes is about 50 nm.
43. The liposomes of any one of embodiments 39-42, wherein the liposomes have an average diameter of 100 nanometers or less.
45. A population of liposomes comprising a sterol in amount of at least 30 mole percent, wherein the average diameter of the liposomes is less than 100 nm.
46. The liposomes of embodiment 44, wherein the average diameter of the liposomes is less than 75 nm.
47. The liposomes of embodiment 44, wherein the average diameter of the liposomes is less than 55 nm.
48. The liposomes of any one of embodiments 44-47, wherein the liposomes are small unilamellar vesicles.
49. The liposomes of any one of embodiments 44-48, wherein the liposomes further comprise an amphiphilic lipid, a (polyethylene glycol)-lipid, or a combination thereof.
50. The liposomes of any one of embodiments 44-49, wherein the sterol is cholesterol or a cholesterol derivative.
51. The liposomes of embodiment 49 or embodiment 50, wherein the (polyethylene glycol)-lipid is a (polyethylene glycol)-phosphatidylethanolamine.
52. The liposomes of any one of embodiments 49-51, wherein the amphiphilic lipid is hydrogenated soy phosphatidylcholine, the sterol is cholesterol, and the (polyethylene glycol)-phospholipid is 1,2-distearoyl-sn-glycero-3-phosphoethanolamine-N-[amino(polyethylene glycol)-5K.
53. The liposomes of any one of embodiments 49-52, wherein the liposomes have polyethylene glycol brush densities of >100,000 polyethylene glycol chains per liposome having an average diameter of 100 nm.
54. The liposomes of any one of embodiments 44-53, wherein the liposomes have a polydispersity index of 0.20 or less.
55. The liposomes of embodiment 44, prepared according to method of any one of embodiments 1-26.

Although the foregoing it as been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A system for producing liposomes from a lipid suspension, comprising:
    a filter housing having an inlet and an outlet;
    a filter assembly disposed inside the filter housing, the filter assembly comprising:
        two or more filters disposed in series;
        a panel comprising an orifice disposed between a pair of adjacent filters, wherein an outer surface of the panel surrounding the central orifice is configured to constrict the flow of a lipid suspension between the adjacent filters through the central orifice;
        wherein the orifice has a diameter that is less than an average diameter of the two or more filters; and
        wherein liposomes produced by passing the lipid suspension through the system at a pressure in the filter assembly less than 300 psi, are smaller in diameter and more monodisperse than liposomes produced with the same number of filters not in series.

2. The system of claim 1, further comprising a component to move a lipid suspension through the filter assembly.

3. The system of claim 1, wherein the system has a flow rate of 30 mL/minute or greater.

4. The system of claim 1, wherein the filters comprise alumina-based membranes, polycarbonate-based membranes, polyether sulfone-based membranes, or a combination thereof, wherein the filters have a thickness of 2 microns or greater.

5. The system of claim 1, wherein the diameter of each orifice disposed between adjacent filters is less than or equal to about 70% of the diameter of the filters adjacent to the orifice.

6. The system of claim 1, wherein the filters and filter housing are at ambient temperature during operation of the system, wherein the system has a static volume of 1-1000 microliters.

* * * * *